US012582624B2

United States Patent (12)
Aramini et al.

(10) Patent No.: US 12,582,624 B2
(45) Date of Patent: Mar. 24, 2026

(54) CO-CRYSTAL OF GABAPENTIN, KETOPROFEN AND LYSINE, PHARMACEUTICAL COMPOSITIONS AND THEIR MEDICAL USE

(71) Applicant: DOMPÉ FARMACEUTICI S.P.A., Milan (IT)

(72) Inventors: Andrea Aramini, L'Aquila (IT); Marcello Allegretti, Rome (IT); Gianluca Bianchini, L'Aquila (IT); Samuele Lillini, Cardito (IT); Mara Tomassetti, Naples (IT)

(73) Assignee: DOMPÉ FARMACEUTICI S.P.A., Milan (IT)

( * ) Notice: Subject to any disclaimer, the term of this patent is extended or adjusted under 35 U.S.C. 154(b) by 739 days.

(21) Appl. No.: 17/920,085

(22) PCT Filed: Apr. 21, 2021

(86) PCT No.: PCT/EP2021/060421
§ 371 (c)(1),
(2) Date: Oct. 20, 2022

(87) PCT Pub. No.: WO2021/214158
PCT Pub. Date: Oct. 28, 2021

(65) Prior Publication Data

US 2023/0181507 A1 Jun. 15, 2023

(30) Foreign Application Priority Data

Apr. 21, 2020 (EP) .................................... 20170740

(51) Int. Cl.

| | |
|---|---|
| ***A61K 31/198*** | (2006.01) |
| ***A61K 31/192*** | (2006.01) |
| ***A61K 31/195*** | (2006.01) |
| ***A61P 25/04*** | (2006.01) |

(52) U.S. Cl.
CPC .......... *A61K 31/198* (2013.01); *A61K 31/192* (2013.01); *A61K 31/195* (2013.01); *A61P 25/04* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 2010/0226981 | A1 | 9/2010 | Karabomni et al. |
| 2012/0022117 | A1 | 1/2012 | Gruss et al. |
| 2013/0035315 | A1 | 2/2013 | Hanna et al. |
| 2013/0109674 | A1 | 5/2013 | Leighton et al. |
| 2017/0088553 | A1 | 3/2017 | Grenier et al. |

FOREIGN PATENT DOCUMENTS

| | | |
|---|---|---|
| AU | 2014393490 | 11/2015 |
| CN | 102341098 | 2/2012 |
| CN | 106831456 | 6/2017 |
| EP | 3670889 | 6/2020 |
| EP | 3842408 | 6/2021 |
| GB | 1497044 | 1/1978 |
| SE | BE 882889 | 8/1980 |
| WO | WO 2005/063297 | 7/2005 |
| WO | WO 2008/112325 | 9/2008 |
| WO | WO 2011/075688 | 6/2011 |
| WO | WO2020126088 | 6/2020 |

OTHER PUBLICATIONS

Reddy et al. ((2009), Cocrystals and Salts of Gabapentin: pH Dependent Cocrystal Stability and Solubility, Crystal Growth & Design, 9, 378-385) (Year: 2009).*
Bethune, S.J., "Thermodynamic and Kinetic Parameters That Explain Crystallization and Solubility of Pharmaceutical Cocrystals," Dissertation, University of Michigan, 2009.
Xu, et al., China Pharmacist, 2017, 12, 208-212 (Abstract).
Deng et al. SMC Anesthesiology (2016) 16:12.
Enteshari-Moghaddam et al., Clinical Rheumatology 2019: 38, 2873-2880.
Low back pain and sciatica in over 15s: assessment and management, National Institute for Health and Care Excellence NICE Guidelines 2016.
M. A. Rose, Anaesthesia, 2082, 57, pp. 451-462.
Moore et al, Cochrane Database Syst Rev. Apr. 27, 2014;(4):CD007938.
Quintero, Journal of Experimental Pharmacology 2017:9 13-21.
Bu-Rong Jil Nat. Rev. Drug Discov, Jul. 2014; 13(7): 533-548.
English Translation of BE 882889.
International Search Report for PCT/BP2021/060421.
Jain, et al., Indian Drugs, 1986, 23, 315-329.

* cited by examiner

*Primary Examiner* — Juliet C Switzer
*Assistant Examiner* — Dawanna Shar-Day White
(74) *Attorney, Agent, or Firm* — HUESCHEN AND SAGE

(57) ABSTRACT

The present invention relates to a new co-crystal of Gabapentin, Ketoprofen and Lysine, to pharmaceutical compositions and to their use in the prevention, reduction or treatment of pain and/or inflammation.

16 Claims, 19 Drawing Sheets

CO-CRYSTAL OF GABAPENTIN, KETOPROFEN AND LYSINE, PHARMACEUTICAL COMPOSITIONS AND THEIR MEDICAL USE

The present invention relates to a co-crystal of Gabapentin, Ketoprofen and Lysine, to a process for its preparation, to a pharmaceutical composition comprising said co-crystal and to the use of said co-crystal or pharmaceutical composition in the treatment of acute or chronic pain, in particular in the treatment of neuropathic or inflammatory pain.

BACKGROUND ART

Pain is a sensory and emotional experience usually arising from actual or potential tissue damage.

Pain conditions can be divided in acute and chronic.

Acute pain is a pain that lasts for a short period of time, typically less than 3 months, and is commonly associated with tissue injury, inflammation, a surgical procedure, childbirth, or a brief disease process.

Chronic pain has been recognized as a pain that persists past normal healing time and hence lacks the acute warning function of physiological nociception. Usually pain is classified as chronic when it lasts or recurs for more than 3 months.

Chronic pain may have different etiologies and includes neuropathic pain, chronic inflammatory pain, for example arthritis, or pain of unknown origin, as fibromyalgia and restless leg syndrome.

Chronic neuropathic pain is caused by a lesion or disease of the somatosensory nervous system that provides information about the body including skin, musculoskeletal, and visceral organs. A number of diseases or pathological conditions can cause a damage to the sensory neurons resulting in hyperalgesia or allodynia, such for example in lower back pain, sciatalgia, post-operative pain, cancer pain, phantom limb pain, HIV pain, diabetic neuropathy pain, Herpes Zoster pain or trigeminal neuralgia.

Chronic inflammatory pain is associated to strong inflammation of infectious, autoimmune or metabolic etiology, such as rheumatoid arthritis, and by structural changes affecting bones, joints, tendons, or muscles, such as osteoarthrosis. Therapy of this type of pain usually includes the use of non-steroidal anti-inflammatory drugs, acetaminophen, and other disease-modifying agents.

Because of its complex etiology, the pharmacological treatment of neuropathic pain differs from the treatment of non-neuropathic pain. Guidelines recommend the use of serotonin and norepinephrine reuptake inhibitors, tricyclic antidepressants, anticonvulsants, or topical lidocaine treatment as first-line and second-line medications for the management of neuropathic pain, with opioids usually recommended as second- or third-line therapies (Deng et al. BMC Anesthesiology (2016) 16:12). Acetaminophen and non-steroidal anti-inflammatory drugs are largely ineffective in neuropathic pain.

Neuroinflammation is a physiological/pathological condition characterized by so infiltration of immune cells, activation of glial cells and production of inflammatory mediators in the peripheral and central nervous system.

Recent progress indicates that the development of neuroinflammation of tissue, within the peripheral nervous system (PNS) and central nervous system (CNS), is responsible for generating and sustaining the sensitization of nociceptive neurons leading to chronic pain. Neuroinflammation occurs in the PNS (that is, peripheral nerves and ganglia) and CNS (that is, spinal cord and brain) and is characterized by infiltration of leukocytes and increased production of inflammatory mediators at these sites. The trafficking of different types of leukocytes in the PNS and CNS occurs with different temporal profiles. Neuroinflammation manifests as activation of glial cells, such as Schwann cells in the nerve, satellite glial cells in the ganglia and microglia, and astrocytes and oligodendrocytes in the spinal cord and brain. Activation of glial cells leads to the production of glial mediators that can modulate pain sensitivity.

Neuroinflammation is a local inflammation which means that it is more effective at eliciting and sustaining pain than systemic inflammation, yet it is difficult to detect in clinic. For example, fibromyalgia, a chronic muscle pain condition, was previously regarded as an atypical pain, because no obvious pathologies and inflammation could be detected in affected patients. However, a recent study identified neuropathy of small nerve fibres in patients with fibromyalgia, which could be a result and also a cause of chronic neuroinflammation. Neuroinflammation appears to be permanent in patients with chronic pain but also occurs in non-chronic conditions such as for example post-surgical pain.

The lack of efficacy of currently available therapies in the management of neuroinflammatory conditions call for the identification of novel specific and safe drugs for the treatment of still unmet medical needs associated with acute or chronic neuro-inflammatory processes (Ru-Rung Jil. Nat. Rev. Drug Discov. 2014 July; 13(7): 533-548.

Gabapentin is an anticonvulsant synthetic analogue of the neurotransmitter gamma-aminobutyric acid (GABA) of formula (I)

(I)

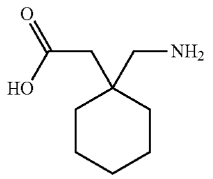

Although its exact mechanism of action is unknown, gabapentin appears to inhibit excitatory neuron activity. The molecule was originally developed as a chemical analogue of gamma-aminobutyric acid to reduce the spinal reflex for the treatment of spasticity but it was found to have no activity on the GABAergic system. Its mechanism of action includes binding to calcium channels in several areas of the central nervous system and spinal cord in which these channels are expressed.

Calcium channels are localized on presynaptic terminals, where they control neurotransmitter release.

Gabapentin was approved for use as an adjunct treatment for partial epileptic seizures in adults and children in 1993. More recently, Gabapentin has also been approved for the treatment of chronic pain, in particular neuropathic pain syndromes. It was also claimed to be beneficial in several other clinical disorders such as anxiety, bipolar disorder, and hot flashes. Gabapentin was also proven effective at high dosage in the treatment of fibromyalgia (Moore et al, Cochrane Database Syst Rev. 2014 Apr. 27; (4):CD007938; Deng et al., BMC Anesthesiology (2016) 16:12).

However, a number of studies have demonstrated an unsatisfactory pharmacological and pharmacokinetic profile when Gabapentin is used alone in pain therapy, for instance in terms of scarce efficacy on specific types of pain, side effects or delayed onset of the response. In fact, Gabapentin is absorbed slowly after oral administration, and it has an utmost level in plasma within 3-4 hours (Quintero, Journal of Experimental Pharmacology 2017:9 13-21).

The plasma level of gabapentin does not increase proportionally if its dosages are increased, thus requiring careful titration on individual basis at the start of a treatment; gabapentin does not attach to plasma proteins.

Gabapentin is neither inhibited nor metabolized by hepatic enzymes; besides, gabapentin can be expelled by the renal system, and its excretion half-life is roughly 6 hours. The most common side effects of gabapentin are somnolence (20%), dizziness (18%), ataxia (13%) and fatigue (11%).

Oral doses of gabapentin are administered three times a day (tds) because of its short half-life. Rapid titration may be achieved with doses of 300 mg once daily (often at bedtime to minimize sedation) on the first day followed by 300 mg twice daily on the second day and 300 mg tds on the third day. Dosage may be further increased if efficacy is not achieved at this dose.

The recommended starting dose in the treatment of neuropathic pain is 300 mg three times a day with titration if necessary to a maximum of 3600 mg·day−1 but doses up to 4200 mg, have been reported when limited or no efficacy is observed (M. A. Rose, Anaesthesia, 2002, 57, pages 451-462).

For example, Gabapentin is not recommended for the treatment of lower back pain because it demonstrates little efficacy together with increased risk of side effects (*Low back pain and sciatica in over* 16*s: assessment and management*, National Institute for Health and Care Excellence NICE Guidelines 2016).

Furthermore, Gabapentin is little active on inflammatory pain, as also confirmed in the present experimental part in the Carrageenan inflammatory rat model.

It was also shown that the therapeutic effect of Gabapentin in the treatment of osteoarthritis starts only after a prolonged administration of 3 months (Enteshari-Moghaddam et al, Clinical Rheumatology 2019: 38, 2873-2880).

The Applicant has undertaken studies to improve the properties of Gabapentin, with the aim of improving the activity of the molecule on pain conditions and extending the efficacy to other pain syndromes and possibly reducing dose related side effects.

In particular, the Applicant has carried out investigations on Gabapentin combined with Ketoprofen, specifically with Ketoprofen Lysine.

Ketoprofen, (RS)-2-(3-benzoylphenyl)-propionic acid, is a well-established nonsteroidal anti-inflammatory drug (NSAID) with analgesic and antipyretic effects of formula II (II)

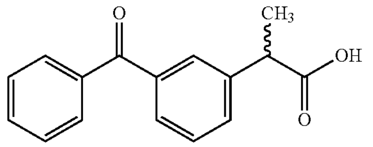

Because of its high tolerability, Ketoprofen is one of the non-steroidal anti-inflammatory drugs of widespread use in clinics, both for the treatment of serious inflammatory conditions and for its use in analgesic and antipyretic by inhibiting the body's production of prostaglandin.

Pharmaceutical compositions of current use containing Ketoprofen have as active ingredient the racemate, where the two enantiomers S(+) and R(−) are present in equimolecular ratio.

Current Ketoprofen pharmaceutical compositions for oral use may contain the active ingredient as free acid which, however, shows a very low solubility in water and therefore a low bioavailability.

In order to improve dissolution profile and bioavailability of the active ingredient, salts of Ketoprofen are also advantageously used.

These salts are used for example in the treatment by oral administration of those pathological symptoms of rheumatoid and chronic type, which require the drug to be administered at high dosage, continuously and for long period of time and in pain manifestation that require an immediate analgesic effect.

In particular, the salt of Ketoprofen with the aminoacid Lysine, although presenting a parallel pharmaceutical profile and a similar anti-inflammatory-analgesic potency compared to the free acid, offers the advantage of a considerably higher solubility in water that enables rapid and almost complete absorption of the compound ensuring a rapid onset of action and a greater gastric tolerability.

Ketoprofen is generally prescribed for arthritis-related inflammatory pains, severe toothaches, treatment of musculoskeletal pain, neuropathic pain such as sciatica, post herpetic neuralgia and referred pain for radiculopathy.

Ketoprofen mechanism of action is essentially based on the inhibition of the biosynthesis of prostaglandins, prostacyclins and thromboxane.

Depending on process conditions, Ketoprofen and Lysine can combine forming either a salt or co-crystals having different crystalline forms (polymorphs) as described in the European Patent Applications n. EP18215336.1 and EP19219293.8 and in the International Patent Application PCT/EP2019/025464.

SUMMARY OF THE INVENTION

The Applicant during these investigations has unexpectedly found that Gabapentin forms a stable co-crystal with Ketoprofen and Lysine.

Furthermore, the Applicant has also found that the new co-crystal shows surprising biological effects.

In this respect, the Applicant has observed a synergistic effect on inflammation and pain when Gabapentin is combined with Ketoprofen and Lysine in the co-crystal.

In fact, when these active ingredients are associated in the co-crystal of the invention, they show an anti-inflammatory and analgesic activity greater than that of Gabapentin when administered in combination with Ketoprofen Lysine.

Additionally, in comparison to Gabapentin alone, a prolongation of the efficacy over time was observed.

Finally, the co-crystal improves dissolution rates of Ketoprofen, especially if dissolving in an aqueous physiological surrounding, and enhances the absorption and/or the bioavailability of the two active molecules.

The solubility and the dissolution rate of drugs are decisive factors related to the rate and extent of absorption after administration.

The higher efficacy of the present co-crystal Ketoprofen-Lysine-Gabapentin, when compared to the co-administration of the separated actives Gabapentin and Ketoprofen Lysine, allows to use of a lower therapeutic dose of either Gabapentin or Ketoprofen, or both and to minimize the side effects.

It is thus an object of the present invention a co-crystal of Gabapentin, Ketoprofen and Lysine wherein the molar ratio of the components is 1:1:1.

The co-crystal is further characterized by the following XRPD diffraction peaks: 3.6, 9.5, 9.6, 18.5 and 20.0 degrees 2-theta±0.2 degrees 2-theta, preferably further characterized by the following XRPD diffraction peaks: 15.4, 17.8, 21.0, 21.8 and 24.2 degrees 2-theta±0.2 degrees 2-theta.

A further object of the present invention is a process for the preparation of the co-crystal of the invention, which comprises:

a) suspending Gabapentin, Ketoprofen and Lysine in a suitable solvent,
b) dissolving Gabapentin, Ketoprofen and Lysine, optionally by heating the suspension, optionally under stirring, till a clear solution is obtained
c) subsequently cooling the solution, and
d) optionally adding an anti-solvent.

A further object of the present invention is a pharmaceutical composition comprising the co-crystal of the invention and at least a pharmaceutically acceptable excipient.

A further object of the present invention is a pharmaceutical composition comprising the co-crystal of the invention and at least another pharmaceutically active ingredient.

A further object of the present invention is the co-crystal of the invention for use as a medicament.

A further object of the present invention is the co-crystal of the invention for use in the treatment of pain and/or inflammation.

A further object of the present invention is a method for the treatment of pain and/or inflammation comprising administering to the patient an effective amount of the co-n crystal of the invention.

DEFINITIONS

For the purpose of the present invention, the term "pharmaceutically acceptable excipient" refers to a substance devoid of any pharmacological effect of its own and which does not produce adverse reactions when administered to a mammal, preferably a human.

For the purpose of the present invention, the term "room temperature" means a temperature range of 18 to 25° C.

For the purpose of the present invention, the term "co-crystal" means a multi-component system, in which all components are solid under ambient conditions when in their pure form. The components coexist at a molecular level within a single crystal. At least some of the components are connected by non-covalent, non-ionic interactions.

For the purpose of the present invention, the term "pain" means pain caused by disturbances of different nature and origin, such as, for example: headache or cephalalgia: both primary and therefore not related to other factors or diseases, and secondary and therefore dependent on trauma, injury and distinct diseases; toothache: in case of abscesses or caries that create pain in the dental pulp, with numerous blood vessels and nerves; menstrual pains: abdominal and lower abdominal pain and headaches caused by hormonal changes typical of the period of menstruation; neuralgia, or intense nerve pain due to strains, trauma and infections: pain in the muscles, or myalgia: pains located at the level of muscles when using or touching them, due to sudden contractions or traumas; osteoarticular pains, such as joint inflammations (to the bones, cartilages, ligaments and tendons) following traumas, old age, strains and injuries.

For the purpose of the present invention, the term "inflammation" means the local response of an organism to cellular injury that is marked by capillary dilatation, leukocytic infiltration, redness, heat, and pain and that serves as a mechanism initiating the elimination of noxious agents and of damaged tissue.

For the purpose of the present invention, the term "anti-solvent" means a solvent in which a compound is insoluble or little soluble.

The terms "approximately" and "about" herein refers to the range of the experimental error, which may occur in a measurement.

Keys in the Figures: GAB Gabapentin; KL Ketoprofen Lysine; Co-xx co-crystal; MIX admixture; KL Co-xx Ketoprofen Lysine co-crystal; K-L-GAB Co-xx Ketoprofen Lysine Gabapentin co-crystal; KL Co-xx® GAB MIX admixture of Ketoprofen Lysine co-crystal with Gabapentin.

DETAILED DESCRIPTION OF THE INVENTION

An object of the present invention is a co-crystal of Gabapentin, Ketoprofen and Lysine wherein the molar ratio of the components is 1:1:1.

Figure 1:
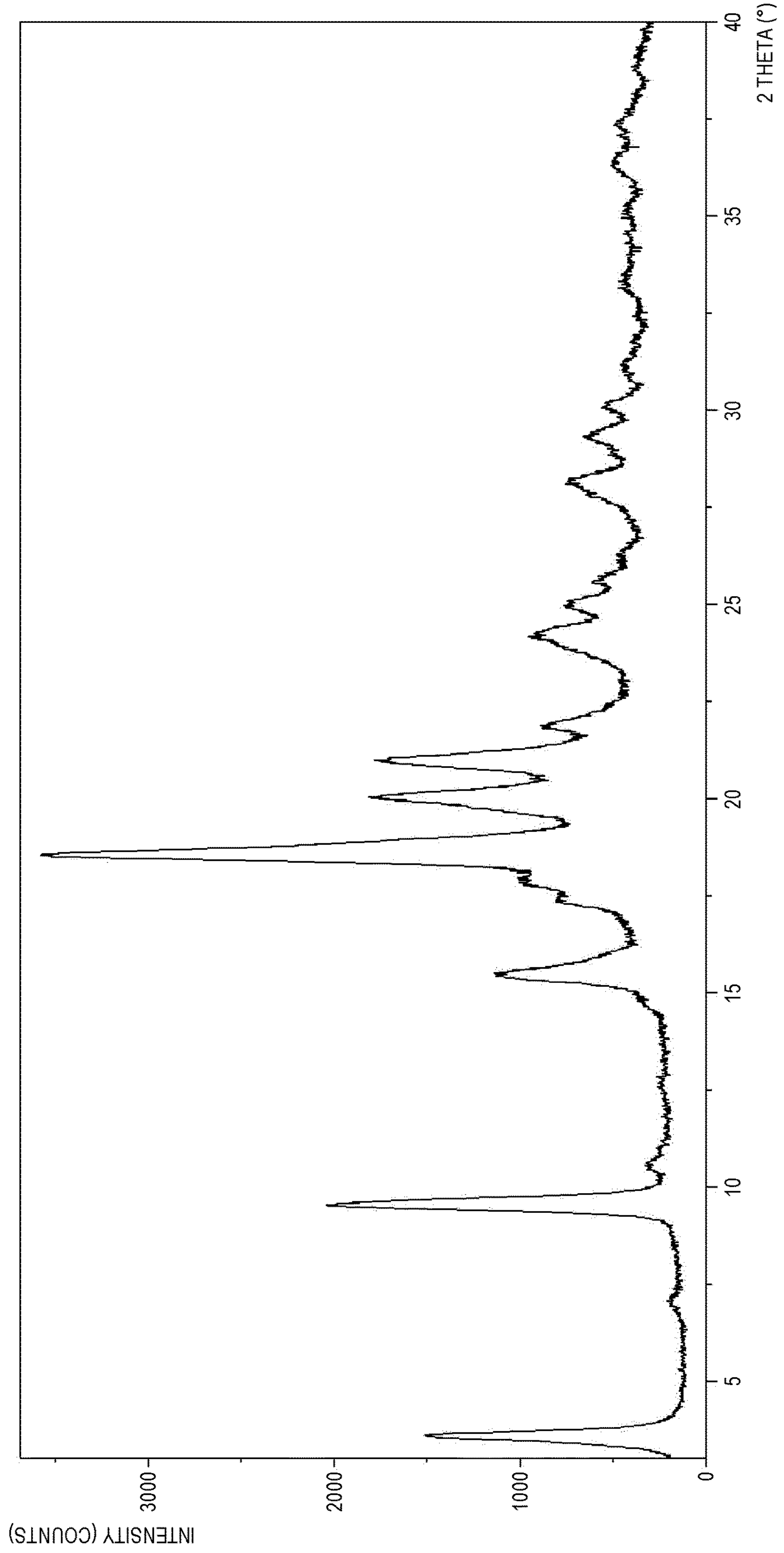
FIG. 1: Powder X-Ray diffraction pattern of Ketoprofen-Lysine-Gabapentin 1:1:1 co-crystal

In line with the solid state $^{13}C$-NMR analysis reported in the experimental part, in the present co-crystal Ketoprofen carboxylic group is deprotonated and interacts with protonated Lysine ε-$NH_3^+$ group through ionic bonds forming a neutral salt. The Ketoprofen Lysine neutral salt interacts with Gabapentin through non-ionic bonds. The co-crystal of the present invention is further characterized by the following XRPD diffraction peaks: 3.6, 9.5, 9.6, 18.5 and 20.0 degrees 2-theta with a margin of error on the value indicated for each peak of ±0.2 degrees 2-theta, preferably further characterized by the following XRPD diffraction peaks: 15.4, 17.8, 21.0, 21.8 and 24.2 degrees 2-theta±0.2 degrees 2-theta, as shown in FIG. 1 and in Table 2.

This crystalline form of the co-crystal of the invention is herein named Form I. Other polymorphs of the present co-crystal are also within the scope of the invention.

Figure 2:
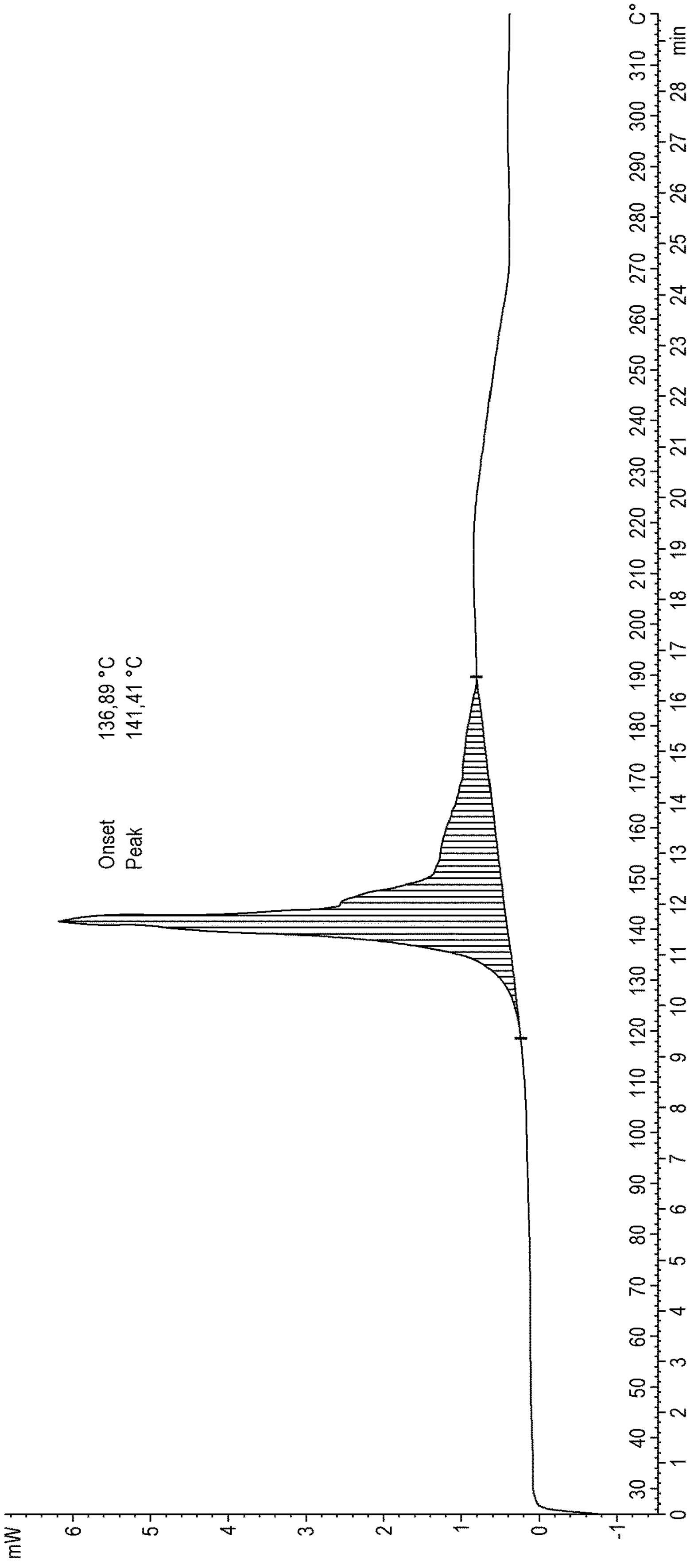
FIG. 2: DSC thermogram of Ketoprofen-Lysine-Gabapentin 1:1:1 co-crystal
Figure 5:
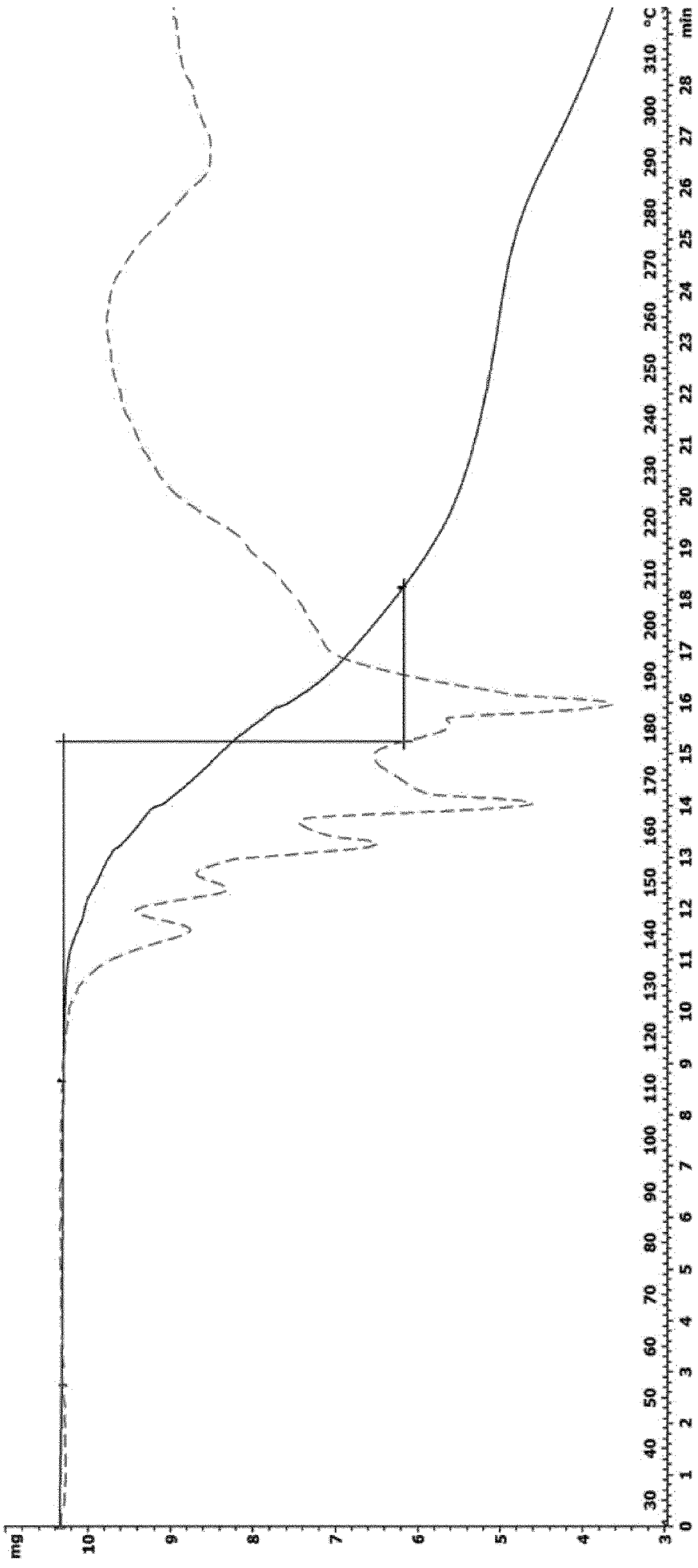
FIG. 5: TG (continuous line) and dTG (dashed line) thermograms of Ketoprofen-Lysine-Gabapentin 1:1:1 co-crystal.
Figure 8:
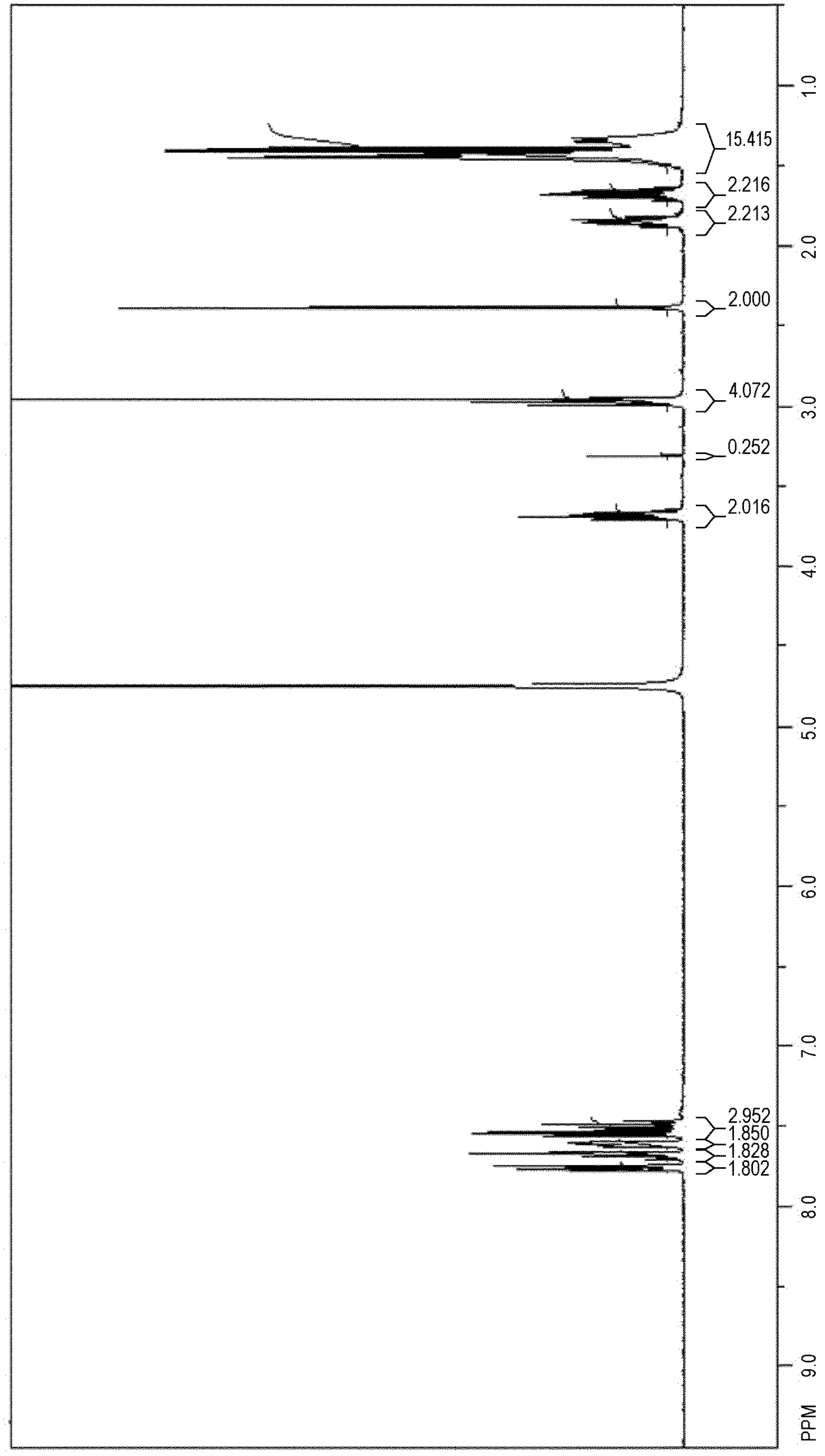
FIG. 8: $^{1}$H-NMR spectrum (400 MHz, $D_2O$) of Ketoprofen-Lysine-Gabapentin 1:1:1 co-crystal.
Figure 9:
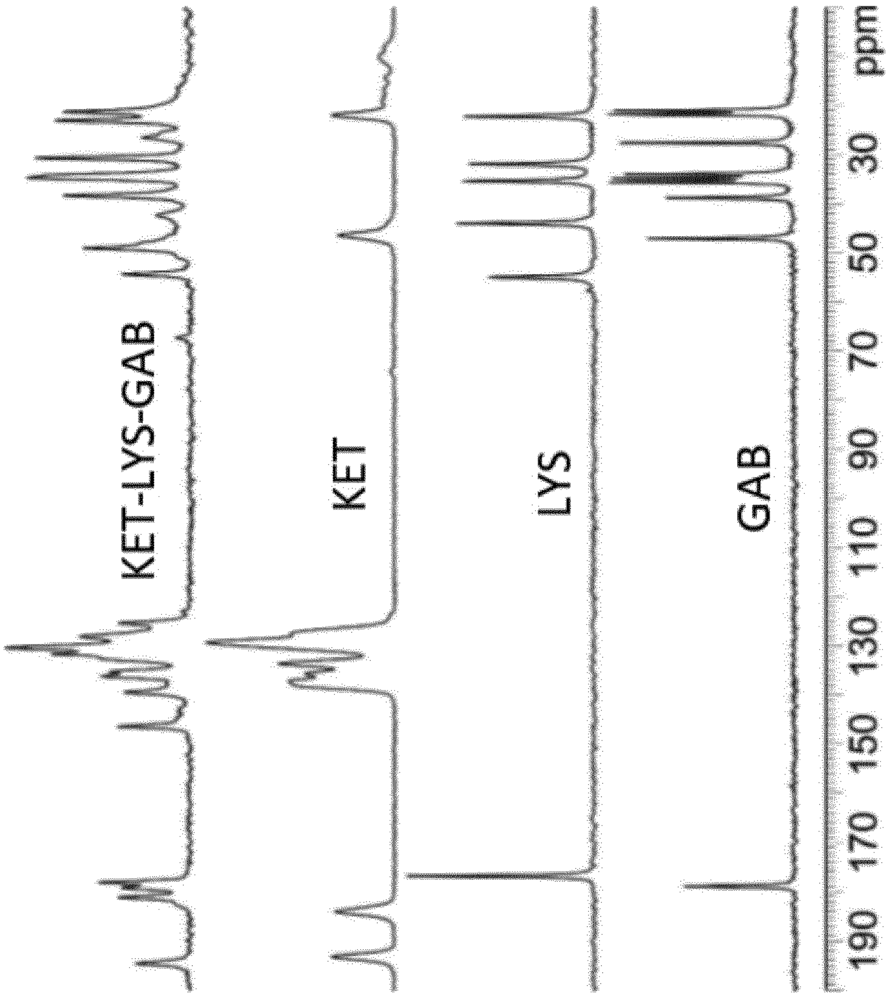
FIG. 9: $^{13}$C CPMAS spectra of Ketoprofen-Lysine-Gabapentin 1:1:1 co-crystal, of Ketoprofen, of Lysine and of Gabapentin.
Figure 10:
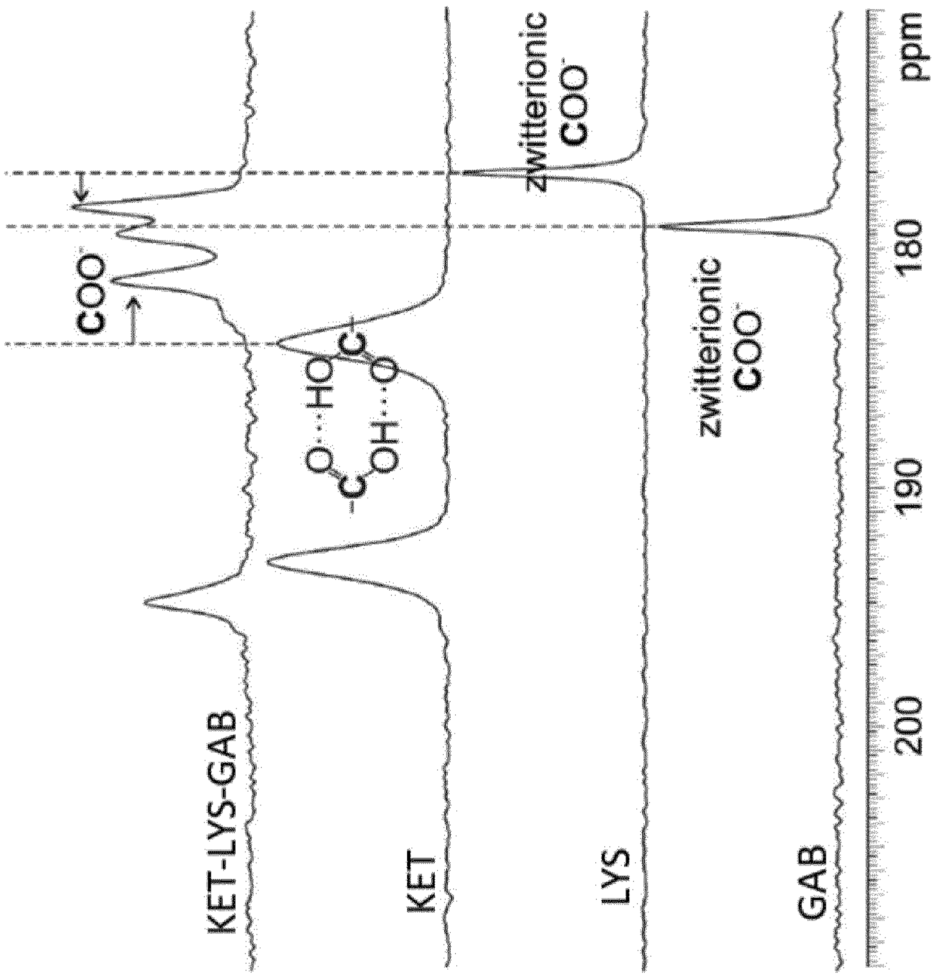
FIG. 10: magnification of the carboxylic region of the $^{13}$C CPMAS spectra of FIG. 9.
Figure 11:
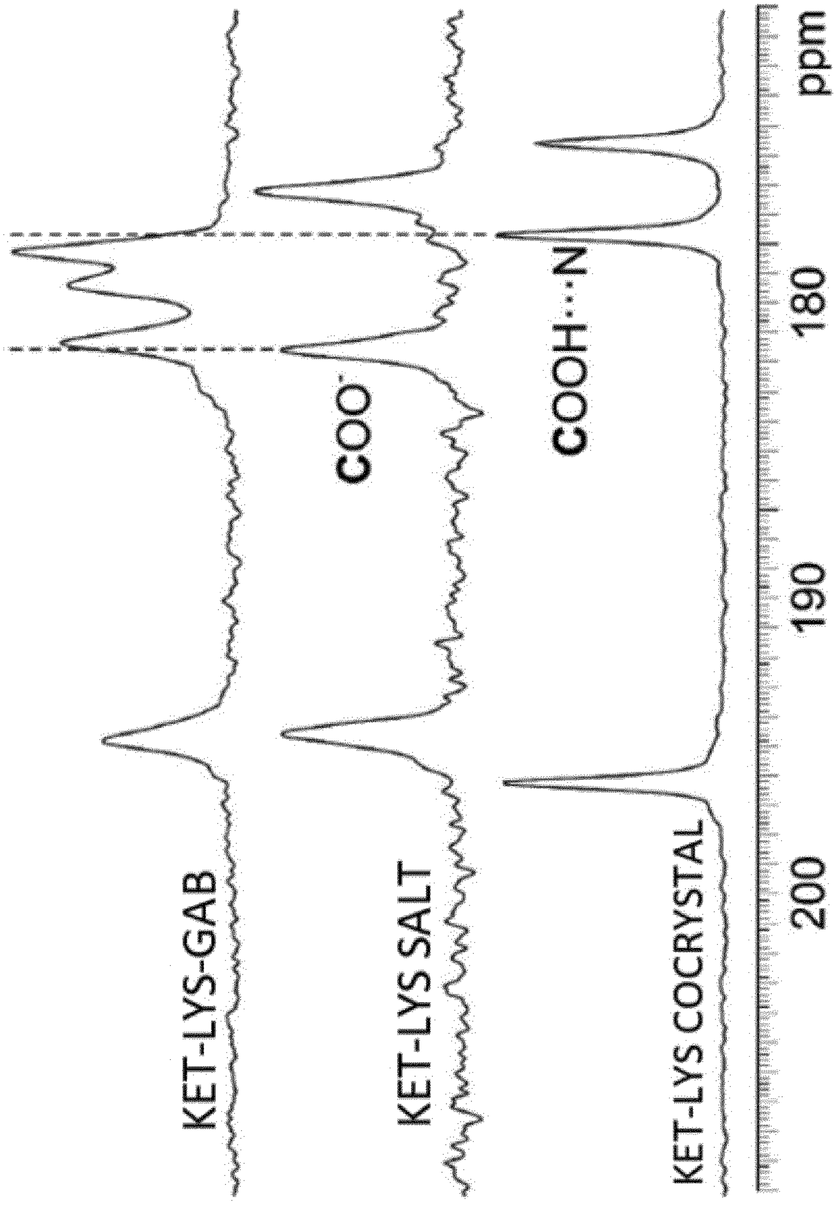
FIG. 11: magnification of the carboxylic region of $^{13}$C CPMAS spectra of Ketoprofen-Lysine-Gabapentin 1:1:1 co-crystal, of Ketoprofen Lysine salt and of Ketoprofen Lysine co-crystal Form I.

The co-crystal of the present invention is further characterized by the DSC thermogram of FIG. 2, with the endothermic sharp peak of the co-crystal corresponding to the melting point at 141.4° C. with an onset at 136.9° C., the TGA thermogram of FIG. 5, FT Raman and FT-IR spectra with typical absorption bands reported in Table 6 and 7, solution $^{1}H$-NMR spectrum of FIG. 8 and relative assignments in Table 8 and/or solid state $^{13}C$ CPMAS of FIGS. 9 to 11 and relative assignments in Table 9.

In the co-crystal of the invention, Ketoprofen can be racemic (S,R) Ketoprofen, (S)-Ketoprofen or (R)-Ketoprofen or any admixture thereof.

In one embodiment Ketoprofen is (S)-Ketoprofen (also named DexKetoprofen).

In another embodiment Ketoprofen is (R)-Ketoprofen.

In the co-crystal of the invention, Lysine can be racemic (S,R) Lysine, (S) Lysine or (R) Lysine, or any admixture thereof, preferably is the natural aminoacid (S)-Lysine also named L-Lysine.

In one embodiment, the co-crystal of the invention comprises (S)-Ketoprofen.

In one embodiment, the co-crystal of the invention comprises (S)-Lysine.

In one embodiment, the co-crystal of the invention comprises (S)-Ketoprofen and (S)-Lysine.

The co-crystal of the present invention can exist in unsolvated forms as well as solvated forms, including hydrated forms.

The co-crystal of the present invention is easily obtainable and stable.

The co-crystal of the present invention would show improved pharmaceutical properties, pharmacokinetics and efficacy in pain conditions, especially when compared to Gabapentin or Ketoprofen alone and surprisingly even when compared to their admixture, as described in the Experimental section that follows.

A further object of the present invention is a process for the preparation of the co-crystal of the invention, which comprises:

a) suspending Gabapentin, Ketoprofen and Lysine in a suitable solvent,
b) dissolving Gabapentin, Ketoprofen and Lysine, optionally by heating the suspension, optionally under stirring, till a clear solution is obtained,
c) subsequently cooling the solution, and
d) optionally adding an anti-solvent.

In the present process, the starting material for Ketoprofen can be Ketoprofen free acid or a Ketoprofen salt, preferably Ketoprofen Lysinate, or any Ketoprofen Lysine co-crystal. In case of Ketoprofen free acid or a Ketoprofen salt different from the Lysinate, Lysine is added, preferably in its neutral form. Lysine is preferably used in the same molar amount of Ketoprofen.

In step a) of the present process, the molar ratio of Gabapentin vs Ketoprofen is preferably between 1:1 and 1.5:1, more preferably between 1:1 and 1.2:1, even more preferably is about 1:1.

In one embodiment, the molar ratio of Gabapentin:Ketoprofen:Lysine in step a) is about 1:1:1.

In the present process, suitable solvents are alcohols, preferably methanol and ethanol, esters, preferably ethyl acetate, ethers, preferably tetrahydrofuran and tert-butylmethyl ether or aromatic solvents, preferably toluene.

Preferably, step b) is performed under heating at the temperature of reflux of the solvent.

Preferably the solution from step b) is cooled at room temperature.

Preferably the solution from step b) is cooled at room temperature and filtered.

Preferably the precipitation of the co-crystal is favored by addition of an anti-solvent. The present process provides the co-crystal of the invention with high yields. It is simple and easy scalable at industrial level.

According to one embodiment, in step a) of the process according to the invention, Ketoprofen and Lysine may be present as a pre-formed salt or co-crystal, in any polymorphic form.

The starting material for the manufacture of the co-crystal of the present invention Gabapentin, Ketoprofen and Ketoprofen Lysine salt or co-crystals may be prepared in accordance with methods of synthesis previously published and well known to the organic chemist of ordinary skill.

Ketoprofen Lysine salt can be prepared as described for instance in GB1497044A and BE882889.

Ketoprofen Lysine co-crystal Form I can be prepared as described for instance in the European Patent Application n. EP18215336.1 or in the International Patent Application PCT/EP2019/025464.

Ketoprofen Lysine co-crystal Form IV can be prepared as described for instance in EP19219293.8.

According to an alternative embodiment, said Ketoprofen is a free acid and/or said Lysine is in neutral form.

In the present preparation process, Gabapentin is preferably used in its neutral form (zwitterionic internal salt) or in any acid or basic salified form, for instance as Gabapentin hydrochloride or Gabapentin Sodium salt.

Preferably, Gabapentin is used in its neutral form.

Gabapentin can be in any polymorph form.

The present invention furthermore relates to a pharmaceutical composition comprising a co-crystal of Ketoprofen-Lysine-Gabapentin according to the present invention, in particular a co-crystal of Ketoprofen-Lysine-Gabapentin as defined above and a least one pharmaceutically acceptable excipient.

For instance, the composition according to the present invention may contain 0.5-60% by weight of the co-crystals as defined herein and 40-99.5% by weight of one or more pharmaceutically acceptable excipients.

The choice of the excipients will to a large extent depend on factors such as the particular mode of administration, the effect on solubility and stability, and the nature of the dosage form.

Pharmaceutical compositions according to the present invention may be in any form suitable for the application to humans and/or animals, preferably humans including infants, children and adults and can be produced by standard procedures known to those skilled in the art.

The pharmaceutical composition of the present invention preferably is an oral solid composition, such as for instance a capsule, pellet, tablet, cachet, chewable dosage forms, powder, lozenge, granules, oral soluble granulate, suspension, emulsion, spray, or as dry powdered form to be reconstituted with a liquid medium.

The pharmaceutical composition can additionally contain one or more pharmaceutically acceptable excipients, such as fillers, binders, glidants, disintegrants, flow regulating agents and release agents.

Suitable excipients are for example disclosed in "Handbook of Pharmaceutical Excipients", 3rd Edition, published by A. H. Kibbe, American Pharmaceutical Association, Washington, USA, and Pharmaceutical Press, London.

Suitable fillers are for example lactose (monohydrate, spray-dried monohydrate, anhydrous and the like), mannitol, xylitol, dextrose, sucrose, sorbitol, microcrystalline cellulose, starch, dibasic calcium phosphate dihydrate and calcium hydrogen phosphate.

Fillers can be present in an amount of 0-80% by weight, preferably in an amount of 10-60% by weight of the total weight of the composition.

Suitable binders are for example polyvinylpyrrolidone, microcrystalline cellulose hydroxypropyl cellulose, hydroxypropyl methylcellulose, methylcellulose, hydroxyethyl cellulose, sugars, dextran, corn starch, gelatin, polyethylene glycol, natural and synthetic gums, pregelatinised starch.

Binders can be present in an amount of 0-80% by weight, preferably in an amount of 10-60% by weight of the total weight of the composition.

Binders are generally used to impart cohesive qualities to a tablet formulation.

Suitable glidants are for example alkaline earth metal salts of fatty acids, like stearic acid such as magnesium stearate, calcium stearate, zinc stearate, sodium stearyl fumarate, and mixtures of magnesium stearate with sodium lauryl sulphate.

The glidant can be present for example in an amount of 0-2% by weight, preferably in an amount of 0.5-1.5% by weight of the total weight of the composition.

Suitable disintegrants are for example croscarmellose sodium, sodium carboxymethyl starch, crosslinked polyvinylpyrrolidone (crosspovidone), sodium carboxymethylglycolate, sodium starch glycolate, sodium carboxymethyl cellulose, calcium carboxymethyl cellulose, polyvinylpyrrolidone, methyl cellulose, microcrystalline cellulose, lower alkyl-substituted hydroxypropyl cellulose, starch, pregelatinised starch, sodium alginate and sodium bicarbonate.

The disintegrant can be present in an amount of 0-20% by weight, preferably in an amount of 1-15% by weight of the total weight of the composition.

A suitable flow regulating agent is for example colloidal silica. The flow regulating agent can be present in an amount of 0-8% by weight, preferably in an amount of 0.1-3% by weight of the total weight of this composition.

A suitable release agent is for example talcum. The release agent can be present in an amount of 0-5% by weight, preferably in an amount of 0.5-3% by weight of the total weight of the composition.

The solid composition may be coated, preferably film coated.

A suitable coating agent are for example cellulose derivatives, poly(meth)acrylate, polyvinyl pyrrolidone, polyvinyl acetate phthalate, and/or shellac or natural rubbers such as carrageenan.

There are many situations in which it will be advantageous or even necessary to deliver the co-crystal of the present invention as a solid, for instance by installing a solid implant composition into suitable body tissues or cavities.

The implant may comprise a matrix of bio-compatible and bioerodible materials in which particles of the co-crystal of the present invention are dispersed, or in which, possibly, globules or isolated cells of a liquid mixture of the present co-crystal are entrapped. Desirably, the matrix will be broken down and completely absorbed by the body. The composition of the matrix is also preferably selected to provide controlled-, sustained-, and/or delayed release of the co-crystal of the present invention over extended periods.

Alternatively, the co-crystal of the invention may be formulated as a solid, semi-solid, or thixotropic liquid for administration as an implanted depot providing modified release of the active compound. Examples of such formulations include The present composition can be administered topically to the skin or mucosa, that is dermally, epidermally, subepidermally or transdermally.

The present composition can be administered sublingually or via a suppository.

Typical formulations for this purpose include pour-on, spot-on, dip, spray, mousse, shampoo, powder formulation, gels, hydrogels, lotions, creams, ointments, dusting powders, dressings, foams, films, skin patches, wafers, implants, depots, sponges, fibres, bandages, microemulsions, orosoluble granulates. Liposomes may also be used.

The pharmaceutical composition of the present invention may be a solid composition for the extemporaneous preparation of a solution for oral or parenteral administration, for example to be administered by intramuscular, intraperitoneal, or intravenous injection.

The pharmaceutical composition of the present invention can be prepared by methods well known to a person skilled in the art.

The composition of the invention may be of immediate-, delayed-, modified-, sustained-, pulsed- or controlled-release type.

According to a further embodiment, the pharmaceutical composition of the invention may comprise the co-crystal of the invention and at least another pharmaceutically active ingredient.

The other pharmaceutically active ingredient will be determined by the circumstances under which the therapeutic agent of the present invention is administered.

A further object of the present invention is the co-crystal of the invention for use as a medicament.

The medical use can be curative, prophylactic or palliative.

The association of the two active ingredients in the same crystal exhibits several advantages for the present medical use.

First, Gabapentin and Ketoprofen Lysine being linked in the co-crystal, often behave as a single chemical entity, thus facilitating the treatments, formulation, dosage etc. Furthermore the two active ingredients are complementing each other in the treatment especially of pain, but possibly also of various other diseases or symptoms.

Another advantage is that the association of two active ingredients into one unique species may allow for a better Pharmacokinetic/Pharmacodynamic (PKPD) including also a better penetration of the blood-brain barrier, which helps in the treatment of pain.

The co-crystal and the composition of the present invention show a synergistic activity of the active ingredients Gabapentin and Ketoprofen Lysine as shown in the present pain and inflammation predictive test.

This unexpected synergy provides enhanced clinical efficacy compared to the individual components of the co-crystal when administered separately, or a reduction in the required dose of each compound, leading to a reduction in side effects whilst maintaining or enhancing the clinical effectiveness of the compounds and treatment.

For example, the patient may experience an improved reduction in the frequency and severity of pain and/or inflammation. Furthermore, the patient may benefit from a longer duration of action from the co-crystal treatment than from treatment with Gabapentin or with Ketoprofen Lysine or with their combination.

It is necessary for the skilled artisan, such as a physician or a veterinarian, not only to determine the preferred route of administration and the corresponding dosage form and amount, but said artisan must also determine the dosing regimen.

The daily dosage for humans and animals may vary depending on factors that have their basis in the respective species or other factors, such as age, sex, weight or degree of illness and so forth.

The daily dosage of the co-crystal according to the invention for humans preferably provides for Ketoprofen acid form in an amount between 25 and 200 mg, preferably between 50 and 150 mg, more preferably of 50 mg, from 1 to 8 times per day, preferably from 1 to 4 times a day, resulting the total Gabapentin amount very low if compared to the normal dosage of Gabapentin alone.

A further object of the present invention is the co-crystal of the invention for use in the treatment of pain and/or inflammation.

The co-crystal and the composition of the present invention are preferably used for the treatment of pain, preferably of acute or chronic pain and inflammation, preferably neuroinflammation.

Preferably, said pain is selected from headache, toothache, menstrual pain, muscle pain, neuropathic pain, diabetic, neuropathy, pain associated to neuroinflammation, cancer pain, osteoarthritis, low back pain, sciatalgia, fibromyalgia, trigeminal neuralgia; post-surgical and post-operative pain, post herpetic neuralgia, rheumatoid arthritis, ankylosing spondylitis, frozen shoulder, phantom limb pain or HIV pain.

A further object of the present invention is a method for the treatment of pain and/or inflammation comprising administering to a patient an effective amount of the co-crystal of the invention.

EXPERIMENTAL PART

In the following, the manufacture of the co-crystal of Gabapentin, Ketoprofen and Lysine, its analytical and biological characterization are described.

1. Synthesis of the Co-Crystal Ketoprofen-Lysine-Gabapentin

Ketoprofen Lysine co-crystal Form I (3.028 g, 1.05 eq.), prepared as described in the European Patent Application n. EP18215336.1 or in the International Patent Application PCT/EP2019/025464 and Gabapentin (1.233 g, 1.0 eq.) were dissolved in 60 ml of boiling methanol. The clear solution was allowed to cool at room temperature, polish-filtered (0.45 μm HPLC filter) and then added to 240 ml of THF under stirring. The solid precipitation took place in approximatively 30 minutes and the suspension was stirred at 25° C. for 5 hours (300 rpm). The solid product was isolated by vacuum filtration on a paper filter, washed with methanol (2×3 ml) and then squeezed under a nitrogen flow for approximatively 10 minutes. The solid was gently ground and then dried at 40° C. and 30 mbar overnight affording 3.57 grams of the desired product as a white solid (Yield: 87%).

2. XRPD Analysis

The XRFD analysis was carried out with the following instrument and under the conditions reported in Table 1 below:

TABLE 1

| | |
|---|---|
| Instrument type: | Rigaku MiniFlex600 |
| Application SW: | Minifiex Guidance |
| Measurement Details | |
| Measurement type: | Single scan |
| Sample mode: | Reflection |

TABLE 1-continued

| Scan | |
|---|---|
| Scan range: | 3.000-40.000° (2θ) |
| Step size: | 0.01° (2θ) |
| Speed: | 10.0°/min (2θ) |
| Scan mode: | Continuous |
| | Used wavelength |
| Intended wavelength type: | Kα1 |
| Kα1: | 1.540598 Å |
| Kα2: | 1.544426 Å |
| Kα2/Kα1 intensity ratio: | 0.50 |
| Kα: | 1.541874 Å |
| Kα: | 1.392250 Å |
| | Instrument Details |
| | X-Ray Generator |
| Tube output voltage: | 40 kV |
| Tube output: | 15 mA |
| High-voltage generation method: | High-frequency Cockcroft-Walton method |
| Stability: | Within ±0.05% for both the tube voltage and tube current, with reference to ±10% of input power variation. |
| | X-ray tube |
| Name: | Toshiba Analix type A-26L |
| Anode material: | Cu |
| Maximus output: | 0.60 kW |
| Focus size: | 1 × 10 mm |
| | Kβ Filter |
| Name: | Ni-filter |
| Thickness (mm): | 0.015 |
| Material: | Ni |
| | Goniometer (Angle measuring device) |
| Type: | Vertical θ/2θ |
| Goniometer radius: | 150 mm |
| Scanning axis: | 0/2θ linked |
| 2θ scanning range: | +2° to +140° |
| 0/2θ axis minimum step angle: | 0.005° (2θ) |
| Position speed: | 500°/min (2θ) |
| Scanning speed: | 0.01 to 100°/min |
| Datum angle: | 2θ = 10° |
| X-ray take-off angle: | 6° (fixed) |
| | Slit |
| DS: | 1.25° |
| IHS: | 10.0 mm |
| SS: | none (open) |
| RS: | none (open) |
| Incident side Soller slit: | 2.5° |
| Receiving side Soller slit: | 2.5° |
| | Detector |
| Name: | D/teX Ultra High-speed 1D Detector |
| Window material: | Be |
| Effective window size: | 13 mm (H) × 20 mm (W) |
| Dimensions: | 80 mm (L) |

The Powder X-Ray diffractogram of Ketoprofen-Lysine-Gabapentin 1:1:1 co-crystal is reported in FIG. 1.

The XRPD peak list of the Ketoprofen-Lysine-Gabapentin co-crystal is reported in Table 2 below:

TABLE 2

| XRPD Peak Least Ketoprofen-Lysine-Gabapentin co-crystal | | | | |
|---|---|---|---|---|
| Pos. [°2Th.] | Height [cts] | FWHM [°2Th.] | d-spacing [Å] | Rel. Int. [%] |
| 3.6243 | 1256.24 | 0.1968 | 24.37916 | 44.29 |
| 7.0534 | 51.19 | 0.2362 | 12.53275 | 1.80 |
| 9.5000 | 1801.29 | 0.0590 | 9.30996 | 63.50 |
| 9.6233 | 1516.24 | 0.1574 | 9.19092 | 53.45 |

TABLE 2-continued

| XRPD Peak Least Ketoprofen-Lysine-Gabapentin co-crystal | | | | |
|---|---|---|---|---|
| Pos. [°2Th.] | Height [cts] | FWHM [°2Th.] | d-spacing [Å] | Rel. Int. [%] |
| 10.4680 | 79.87 | 0.2755 | 8.45111 | 2.82 |
| 12.6639 | 20.59 | 0.3149 | 6.99015 | 0.73 |
| 15.3950 | 747.19 | 0.1771 | 5.75573 | 26.34 |
| 17.3403 | 289.20 | 0.1968 | 5.11416 | 10.20 |
| 17.7614 | 424.90 | 0.1574 | 4.99385 | 14.98 |
| 18.4902 | 2836.52 | 0.2165 | 4.79862 | 100.00 |
| 20.0384 | 1179.99 | 0.1378 | 4.43123 | 41.60 |
| 21.0169 | 1119.87 | 0.2362 | 4.22708 | 39.48 |
| 21.8156 | 341.15 | 0.0984 | 4.07409 | 12.03 |
| 24.1842 | 423.80 | 0.3542 | 3.68017 | 14.94 |
| 24.9285 | 267.14 | 0.3149 | 3.57196 | 9.42 |
| 25.5929 | 147.96 | 0.1574 | 3.48072 | 5.22 |
| 26.3078 | 57.71 | 0.2362 | 3.38773 | 2.03 |
| 28.2213 | 282.35 | 0.3542 | 3.16223 | 9.95 |
| 29.3116 | 215.34 | 0.1181 | 3.04704 | 7.59 |
| 30.1350 | 117.37 | 0.2755 | 2.96564 | 4.14 |
| 31.1559 | 65.10 | 0.4723 | 2.87075 | 2.30 |
| 33.1403 | 60.48 | 0.3149 | 2.70325 | 2.13 |
| 35.1961 | 38.04 | 0.3936 | 2.54992 | 1.34 |
| 36.3378 | 93.22 | 0.4723 | 2.47238 | 3.29 |
| 37.3924 | 85.73 | 0.2362 | 2.40505 | 3.02 |
| 38.7653 | 45.33 | 0.2362 | 2.32297 | 1.60 |

3. Thermal Analyses

DSC Analysis

The analysis was carried out using the instrument DSC Mettler Toledo DSC1.

The sample was weighed in an aluminum pan hermetically sealed with an aluminum cover. The analysis was performed by heating the sample from 25° C. to 320° C. at 10K/min, under the conditions shown in Table 3 below:

TABLE 3

| Temperature Data | |
|---|---|
| Temperature range | −40° C. to 450° C. |
| Temperature accuracy | ±0.2 K |
| Temperature precision | ±0.02 K |
| Furnace temperature resolution | ±0.00006 K |
| Heating rate | 0.02 to 300 K/min |
| Cooling rate | 0.02 to 50 K/min |
| Cooling time | 5 min (100° C. to 0° C.) |
| Calorimetric Data | |
| Sensor type | FRS5 |
| Sensor material | Ceramic |
| Number of thermocouples | 56 |
| Signal time constant | 1.8 s |
| Indium peak (height to width) | 17 |
| TAWN resolution | 0.12 |
| Sensitivity | 11.9 |
| Resolution | 0.04 μW |
| Digital resolution | 16.8 million points |

Figure 3:
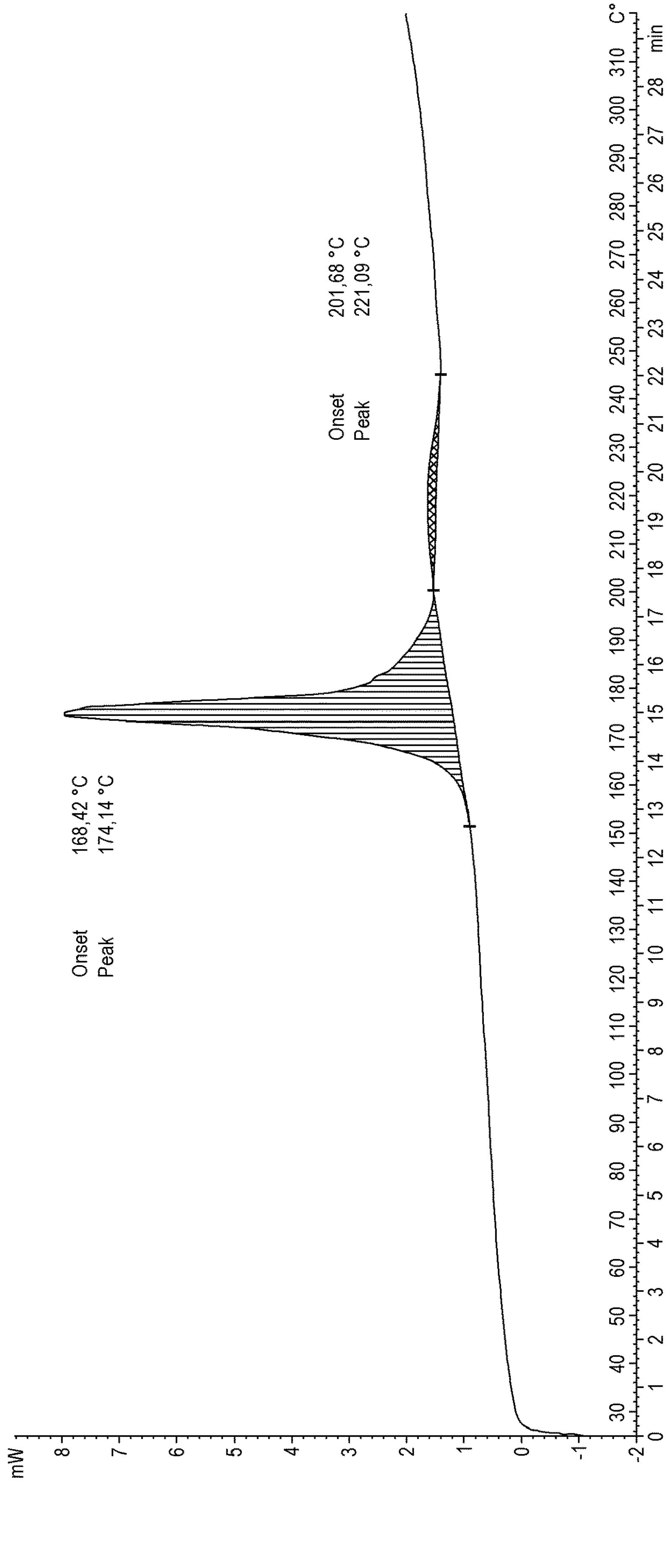
FIG. 3: DSC thermogram of Ketoprofen Lysine co-crystal Form I
Figure 4:
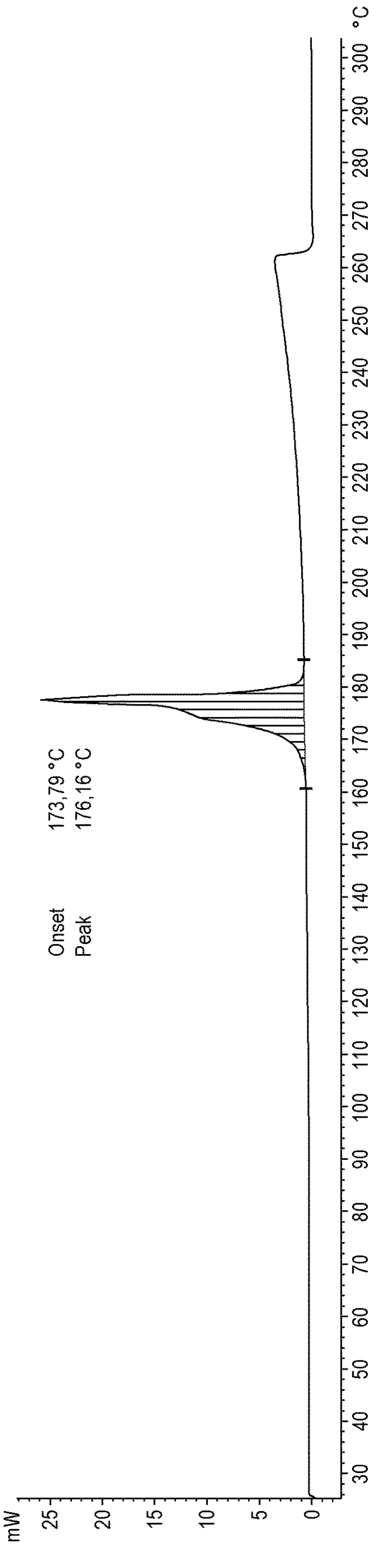
FIG. 4: DSC thermogram of Gabapentin

The analysis was carried out on samples of Ketoprofen-Lysine-Gabapentin co-crystal (FIG. 2), of Ketoprofen Lysine co-crystal Form I (FIG. 3) and of Gabapentin (FIG. 4).

Thermogravimetric Analysis TGA

The analysis was carried out using the instrument Mettler Toledo TGA/DSC1.

The sample was weighed in an aluminum pan hermetically sealed with an aluminum pierced cover. The analysis was performed by heating the sample from 25° C. to 320° C. at 10°/min, under the conditions shown in Table 4 below:

TABLE 4

| Temperature Data | |
|---|---|
| Temperature range | RT to 1100° C. |
| Temperature accuracy | ±1 K |
| Temperature precision | ±0.4 K |
| Heating rate | 0.02 to 250 K/min |
| Cooling time | 20 min (1100 to 100° C.) |
| Sample volume | ≤100 μL |
| Special modes | |
| Automation | 34 sample positions |
| TGA-FTIR | coupled with Thermo Nicolet iS10 spectrometer |
| Balance data | XP5 |
| Measurement range | ≤5 g |
| Resolution | 1.0 μg |
| Weighing accuracy | 0.005% |
| Weighing precision | 0.0025% |
| Internal ring weights | 2 |
| Blank curve reproducibility | better than ±10 μg over the whole temperature range |

Figure 6:
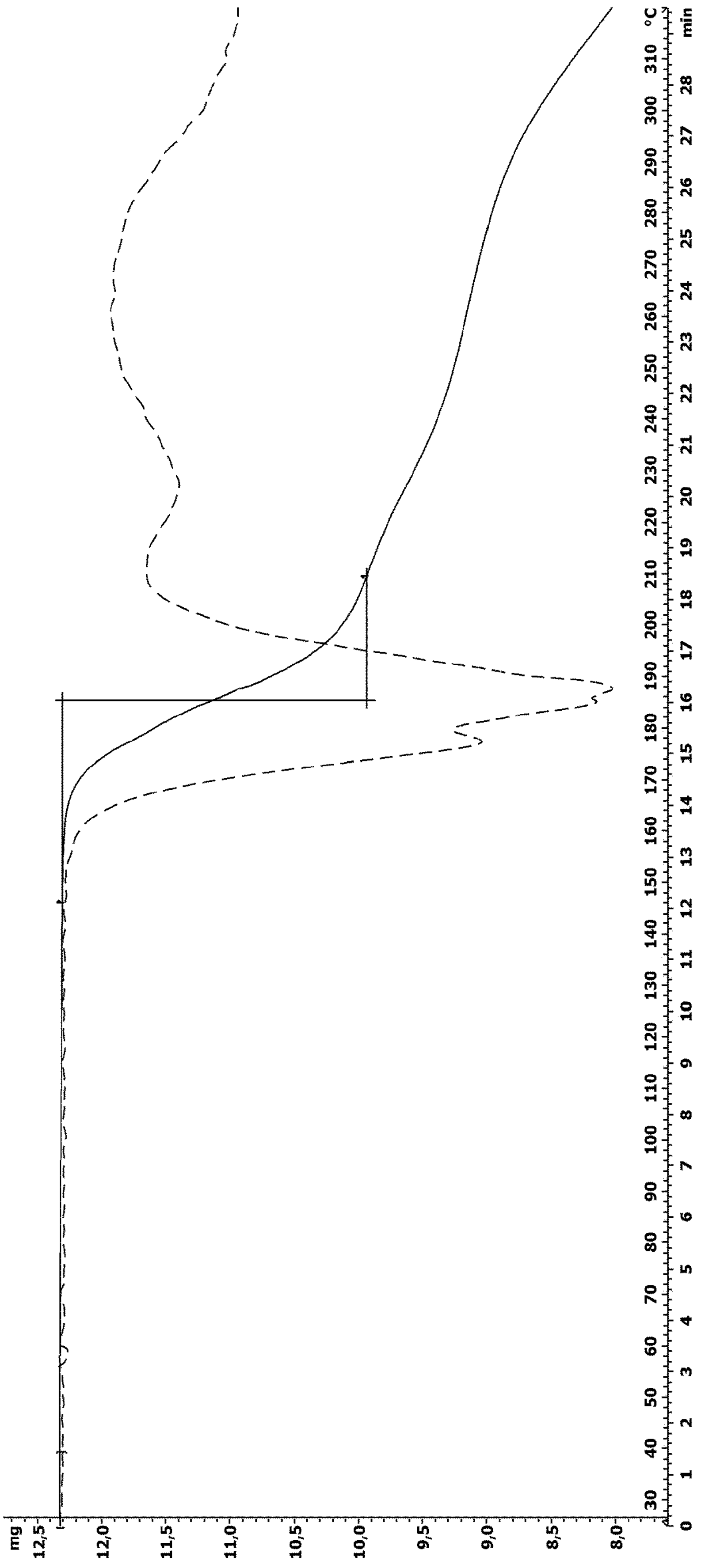
FIG. 6: TG (continuous line) and dTG (dashed line) thermograms of Ketoprofen Lysine co-crystal Form I
Figure 7:
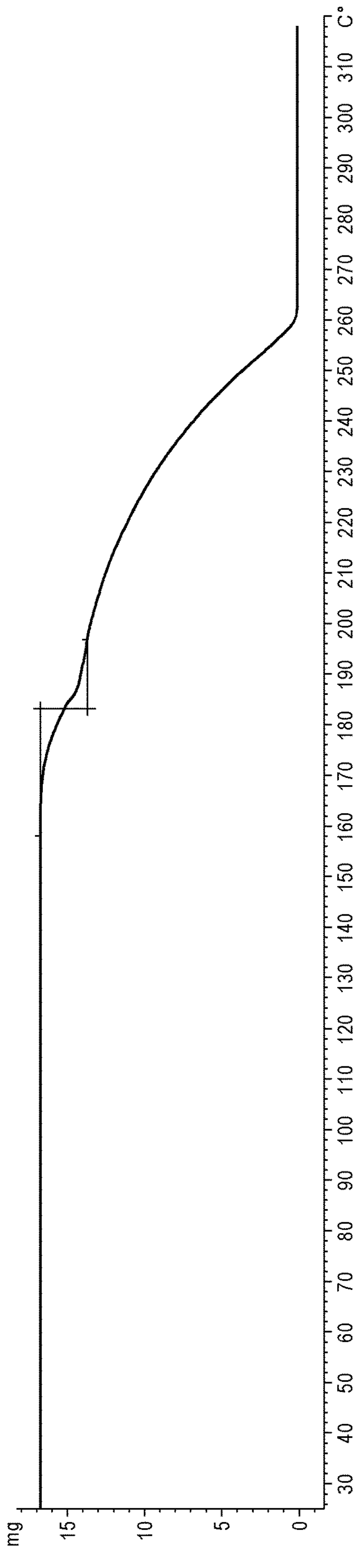
FIG. 7: TG thermogram of Gabapentin

The TG analysis was carried out on samples of Ketoprofen-Lysine-Gabapentin co-crystal (FIG. 5, sample 10.33 mg, left limit 113.90° C., right limit 211, 31° C.), of Ketoprofen Lysine co-crystal Form I (FIG. 6, sample 12.32 mg, left limit 144.51° C., right limit 207.29° C.) and of Gabapentin (FIG. 7, sample 16.67 mg, left limit 160.49° C., right limit 198.27° C.). FIGS. 5 and 6 show both the TG (solid line) and dTG (dotted line) thermograms obtained for the samples.

The TG analysis of the Ketoprofen-Lysine-Gabapentin co-crystal 1:1:1 according to the invention does not show weight loss at temperatures below the melting point (see FIG. 4).

Evolution Gas Analysis (EGA)

EGA analysis was carried out on a sample of Ketoprofen-Lysine-Gabapentin co-crystal.

The DSC thermogram of FIG. 2 showed a single endothermic event at 141.4° C. (onset 136.9° C.), associated to sample melting and degradation. This peak was clearly different from the endothermic peaks of the thermograms of Gabapentin and Ketoprofen Lysine co-crystal Form I shown in FIG. 3.

The TG analysis of 1:1:1 Ketoprofen-Lysine-Gabapentin co-crystal confirmed the presence of an anhydrous compound (FIG. 5).

The EG analysis showed the presence in the evolved gas of the characteristic degradation products of both Gabapentin and Ketoprofen Lysine co-crystal Form I (Figure not shown).

4. FT-Raman and FT-IR

FT-Raman

Raman spectra were recorded with a Nicolet iS50 FT-IR Spectrometer. The excitation source was an Nd-YAG laser (1064 nm) in the backscattering (180°) configuration. The focused laser beam diameter was approx. 50 mm and the spectral resolution 4 $cm^{-1}$. The spectra were recorded with a laser power at the sample of approx. 100 mW.

FT-IR

The analysis was carried out using an instrument Thermo Nicolet iS50-ATR module Spectrometer equipped with Smart Performer Diamond, DTGS KBr Detector, IR Source, KBr Beam splitter, under the conditions shown in Table 5 below:

TABLE 5

| Data Collection Information | |
|---|---|
| Number of sample scans: | 32 |
| Number of background scans: | 32 |
| Collection length: | 47.29 sec |
| Resolution: | 4.000 |
| Levels of zero filling: | 2 |
| Number of scan points: | 16672 |
| Number of FFT points: | 65536 |
| Laser frequency: | 15798.3 cm−1 |
| Interferogram peak position: | 8192 |
| Apodization: | N-B strong |
| Phase correction: | Mertz |
| Number of background scans: | 32 |
| Background gain: | 1.0 |
| Sample gain: | 8 |
| Aperture | 100 |
| Optical velocity | 0.6329 |

The peak list of the Raman spectrum of Ketoprofen-Lysine-Gabapentin co-crystal is reported in Table 6 below:

TABLE 6

Raman peak list of Ketoprofen-Lysine-Gabapentin co-crystal

| Position ($cm^{-1}$) | Intensity |
|---|---|
| 272 | 14.482 |
| 290 | 15.262 |
| 350 | 8.548 |
| 373 | 9.146 |
| 410 | 12.010 |
| 507 | 9.469 |
| 618 | 16.350 |
| 711 | 18.962 |
| 723 | 15.118 |
| 759 | 9.965 |
| 783 | 8.629 |
| 820 | 8.798 |
| 884 | 15.143 |
| 912 | 10.347 |
| 976 | 15.373 |
| 1001 | 116.397 |
| 1032 | 22.031 |
| 1056 | 15.102 |
| 1265 | 15.288 |
| 1281 | 19.151 |
| 1315 | 17.851 |
| 1346 | 12.275 |
| 1362 | 12.462 |
| 1396 | 15.608 |
| 1449 | 40.732 |
| 1490 | 8.848 |
| 1598 | 97.480 |
| 1652 | 58.327 |
| 2723 | 9.298 |
| 2771 | 11.471 |
| 2863 | 55.705 |
| 2929 | 93.607 |
| 2967 | 51.194 |
| 3005 | 21.687 |
| 3064 | 78.264 |

The peak list of the FT-IR spectrum of the Ketoprofen-Lysine-Gabapentin co-crystal is reported in Table 7 below:

TABLE 7

| FT-IR peak list of Ketoprofen-Lysine-Gabapentin co-crystal | |
|---|---|
| Position ($cm^{-1}$) | Intensity |
| 420 | 61.320 |
| 479 | 86.959 |
| 496 | 84.511 |
| 508 | 83.197 |
| 556 | 78.060 |
| 579 | 84.959 |
| 603 | 85.297 |
| 619 | 82.829 |
| 641 | 75.429 |
| 654 | 84.715 |
| 691 | 65.138 |
| 700 | 62.820 |
| 709 | 62.038 |
| 741 | 86.760 |
| 777 | 84.071 |
| 828 | 88.929 |
| 841 | 90.789 |
| 881 | 80.755 |
| 910 | 87.977 |
| 928 | 88.449 |
| 944 | 88.718 |
| 963 | 87.854 |
| 999 | 90.389 |
| 1028 | 89.041 |
| 1060 | 86.249 |
| 1076 | 87.549 |
| 1089 | 86.128 |
| 1114 | 90.673 |
| 1142 | 85.854 |
| 1158 | 83.571 |
| 1179 | 85.407 |
| 1204 | 85.563 |
| 1243 | 72.908 |
| 1281 | 63.418 |
| 1317 | 73.752 |
| 1359 | 64.089 |
| 1391 | 54.270 |
| 1426 | 78.288 |
| 1450 | 71.708 |
| 1474 | 67.220 |
| 1501 | 58.164 |
| 1508 | 57.858 |
| 1542 | 63.709 |
| 1578 | 74.234 |
| 1596 | 77.930 |
| 1628 | 69.686 |
| 1649 | 74.257 |
| 2600 | 83.830 |
| 2850 | 79.325 |
| 2929 | 76.320 |

5. Liquid and Solid State NMR $^{1}H$-Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, br=broad. Coupling constants (J values) are given in hertz (Hz).

The solid-state $^{13}C$ CPMAS spectra of Ketoprofen-Lysine-Gabapentin and pure so Gabapentin were acquired with a Jeol ECZR 600 instrument, operating at 600.17 and 150.91 MHz, respectively for $^{1}H$ and $^{13}C$ nuclei. The powder samples were packed into a cylindrical zirconia rotor with a 3.2 mm o.d. and a 60 μl volume. A sample was collected from each batch and used without further preparations to fill the rotor. The $^{13}C$ CPMAS spectra were acquired at room temperature, at a spinning speed of 20 kHz, using a ramp cross-polarization pulse sequence with a 90° $^{1}H$ pulse of 2.1 μs and a contact time of 3.5 ms. An optimized recycle delay of 5.7 (Ketoprofen-Lysine-Gabapentin) or 100 s (GAB) was used, for a number of scans of 2200 (Ketoprofen-Lysine-Gabapentin) or 20 (GAB). For every spectrum, a two-pulse phase modulation (TPPM) decoupling scheme was used, with a radiofrequency field of 108.5 kHz. The $^{13}C$ chemical shift scale was calibrated through the methylene signal of external standard glycine (at 43.7 ppm). As for the $^{13}C$ $T_1$-$^{1}H$ analysis, 12 spectra were acquired for 350 scans with different relaxation delays, included in the range 0.1-60 s and calculated by the Delta v5.2.1 software through an exponential algorithm. The spectra were acquired at a spinning speed of 20 kHz at room temperature using a ramp cross-polarization pulse sequence with a 90° $^{1}H$ pulse of 2.1 μs and a contact time of 2 ms.

$^{1}H$-NMR Spectra of Co-Crystal Ketoprofen-Lysine-Gabapentin $^{1}H$-NMR spectrum of Ketoprofen-Lysine-Gabapentin co-crystal confirmed the concomitant presence in the sample of Ketoprofen-Lysine-Gabapentin with 1:1:1 stoichiometry. Traces of residual methanol could be detected as well (approx. 0.2% w/w).

The multiplicity and the assignment of the signals in line with the atoms numbering shown in Scheme 1

Scheme 1

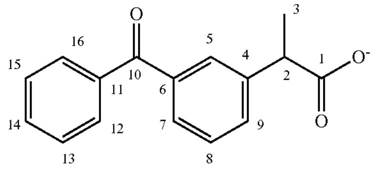

Ketoprofen

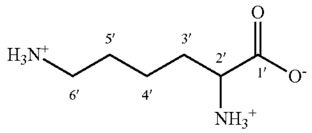

Lysine

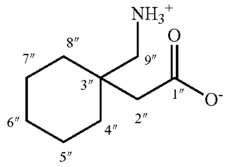

Gabapentin are reported in Table 8 below:

TABLE 8

| $^{1}H$-NMR | | |
|---|---|---|
| δ ppm | Multiplicity | Assignment |
| 7.76-7.78 | m, 2H | Ar KET |
| 7.68-7.72 | m, 2H | Ar KET |
| 7.60-7.63 | m, 2H | Ar KET |
| 7.47-7.57 | m, 3H | Ar KET |
| 3.70 | t, J = 6.4 Hz, 1H | CH (2') LYS |
| 3.69 | quart., J = 7.2 Hz, 1H | CH (2) KET |

TABLE 8-continued

| $^1$H-NMR | | |
|---|---|---|
| δ ppm | Multiplicity | Assignment |
| 2.98 | t, J = 7.6 Hz, 2H | $CH_2$ (6') LYS |
| 2.96 | s, 2H | $CH_2$ (9") GAB |
| 2.38 | s, 2H | $CH_2$ (2") GAB |
| 1.79-1.92 | m, 2H | $CH_2$ (5') LYS |
| 1.68 | quint., J = 7.6 Hz, 2H | $CH_2$ (3') LYS |
| 1.40 | d, J = 7.2 Hz, 3H | CH3 (3) KET |
| 1.29-1.52 | m, 12H | 5 $CH_2$ (4", 5", 6", 7", 8") GAB; $CH_2$ (4') LYS |
| Ratio KET:LYS:GAB 1:1:1 | | |

The $^1$H-NMR spectrum (400 MHz, $D_2O$) of Ketoprofen-Lysine-Gabapentin co-crystal is shown in FIG. 6.

Solid State $^{13}$C CPMAS Spectra of Co-Crystal Ketoprofen-Lysine-Gabapentin

A new homogeneous phase of Ketoprofen-Lysine-Gabapentin was confirmed by $^{13}$C-CPMAS spectra. The stoichiometry was assessed to be 1:1:1, with one independent molecule of Ketoprofen, Lysine and Gabapentin in the unit cell.

Ketoprofen carboxylic group is deprotonated and interacts with protonated Lysine $NH_3^+$ group through ionic bonds forming a neutral salt. The Ketoprofen Lysine neutral salt interacts with Gabapentin through non-ionic bonds forming a co-crystal. Both Lysine and Gabapentin are in a zwitterionic state in the new crystal form.

In Table 9 below the characteristic solid state $^{13}$C NMR resonances are summarized:

TABLE 9

| solid state $^{13}$C NMR | |
|---|---|
| $^{13}$C δ (ppm) | Assignment |
| 194.7 | 10 |
| 181.2 | 1 |
| 179.3 | 1" |
| 178.2 | 1' |
| 146.4 | Aromatic $C_q$ |
| 139.5 | Aromatic $C_q$ |
| 136.2 | Aromatic $C_q$ |
| 135.3 | Aromatic CH |
| 132.6 | Aromatic CH |
| 131.7 | Aromatic CH |
| 130.4 | 3 Aromatic CH |
| 128.1 | 2 Aromatic CH |
| 125.4 | Aromatic CH |
| 54.4 | 2' |
| 49.0 | 9" |
| 48.0 | 2 |
| 42.3 | 6' |
| 38.4 | 2" + 4" or 8" |
| 34.7 | 3' + 4" or 8" |
| 34.3 | 6" |
| 30.7 | 5' + 3" |
| 26.6 | 4' |
| 25.5 | 3 |
| 23.1 | 5" or 7" |
| 21.3 | 5" or 7" |

FIG. 7 displays the $^{13}$C CPMAS NMR spectra of Ketoprofen-Lysine-Gabapentin co-crystal and of the separated starting materials, namely Ketoprofen (KET), Lysine (LYS) and Gabapentin (GAB).

All signals in the spectrum of Ketoprofen-Lysine-Gabapentin co-crystal are characterized by similar $^1$H $T_1$ values (around 6.5 s), meaning that spin diffusion is active among the molecules of Ketoprofen, Lysine and Gabapentin, i.e. the three molecules are in the same unit cell. In FIG. 10, the magnification of the carboxylic region is shown.

In this magnified region three distinct resonances for carboxylic/carboxylate groups were observed suggesting a 1:1:1 stoichiometric ratio for the Ketoprofen-Lysine-Gabapentin system, with one independent molecule for each compound.

Gabapentin is a zwitterion in its pure Form II polymorph: its carboxylate group stays deprotonated in Ketoprofen-Lysine-Gabapentin with a minimal shift towards higher frequencies, which indicates the chemical environment of the $COO^-$ moiety of Gabapentin is very similar between the adduct and the pure reagent.

The zwitterionic carboxylate of Lysine undergoes a shift from 176.7 ppm in pure Lysine to 178.2 ppm in Ketoprofen-Lysine-Gabapentin, probably due to the involvement of the carboxylate group in stronger hydrogen bonds than in the starting material. The Lysine is supposed to be in the zwitterionic form.

Finally, the carboxylic group of Ketoprofen, which is involved in a homodimeric synthon in its pure form, falls at 181.2 ppm in Ketoprofen-Lysine-Gabapentin, decreasing its chemical shift of almost 3 ppm. This strongly suggests the occurrence of a protonic transfer from the COOH moiety of Ketoprofen, which turns into a carboxylate moiety, to the only possible acceptor, the ε-NH2 of Lysine.

FIG. 11 shows a comparison of the carboxylic regions for Ketoprofen-Lysine-Gabapentin co-crystal of the present invention, Ketoprofen Lysine co-crystal (Form I) and Ketoprofen Lysine salt.

The comparison of the signals of FIG. 11 confirms the deprotonation state of the carboxylic moiety of Ketoprofen in Ketoprofen-Lysine-Gabapentin. Indeed, the chemical shift for its corresponding peak is significantly more similar to the one of the carboxylate group of Ketoprofen in Ketoprofen-Lysine salt than to the signal of the neutral hydrogen bonded COOH group of Ketoprofen in the co-crystal Ketoprofen-Lysine.

6. Solubility Test

The solubility assays were performed using an automatic potentiometric titrator using SiriusT3 apparatus (Pion Inc. Ltd., East Sussex, UK) equipped with an Ag/AgCl double junction reference pH electrode, a Sirius D-PAS spectrometer and a turbidity sensing device. The pH electrode was calibrated titrimetrically in the pH range 1.8-12.2. An overhead stirrer was used, and a temperature probe monitored the temperature during the course of the assay. The solubility experiments were conducted in 1.5 ml of 0.15 M KCl solution (ISA water) under a nitrogen atmosphere at a temperature of 25±1° C. All tests were performed using standardized 0.5 M KOH and 0.5 M HCl as titration reagents. The solubility assays were performed, by weighing 15-20 mg of powder samples, the samples stirred at 800 rpm and automatically titrated from pH 11 to pH 1.5.

Figure 12:
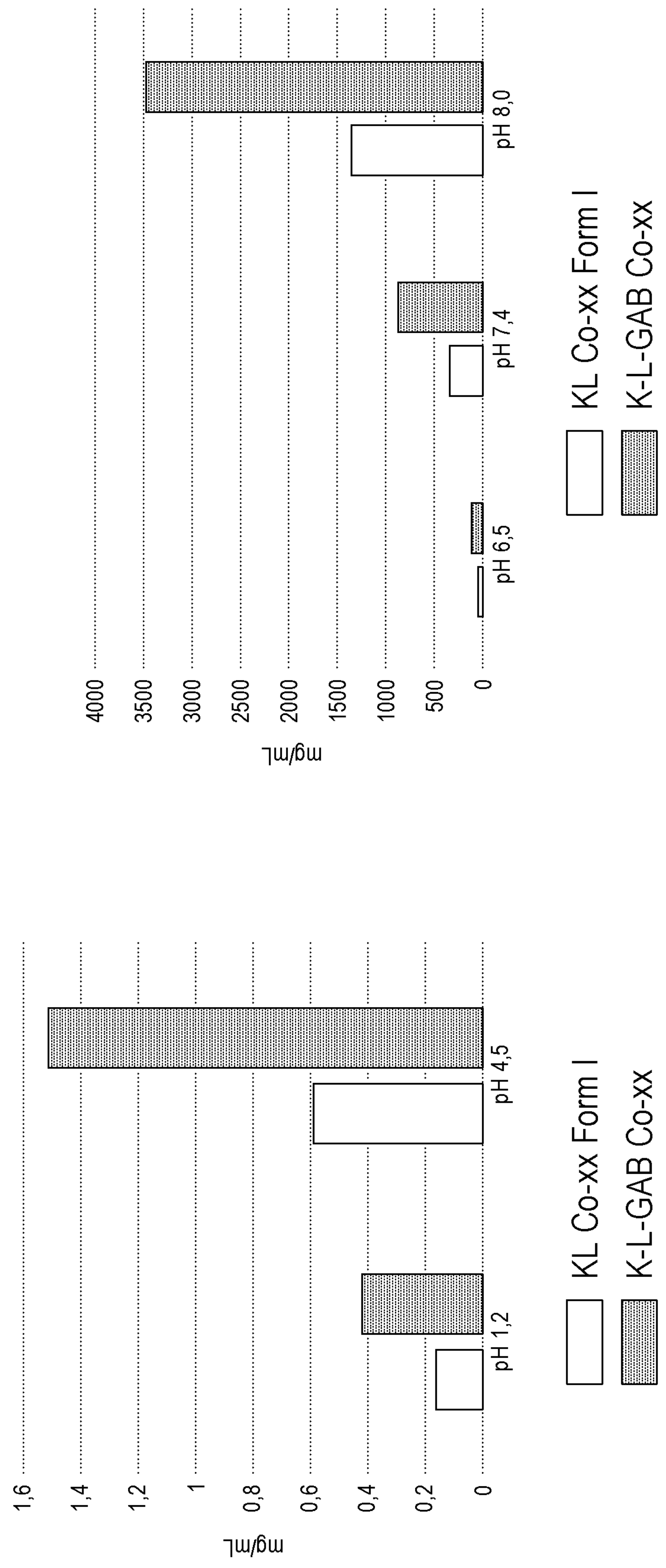
FIG. 12: solubility at different pH of Ketoprofen-Lysine-Gabapentin 1:1:1 co-crystal and Ketoprofen Lysine co-crystal Form I.

Solubility of Ketoprofen Lysine Co-Crystal Form I and Ketoprofen-Lysine-Gabapentin Co-Crystal The solubility of Ketoprofen Lysine co-crystal Form I and Ketoprofen-Lysine-Gabapentin co-crystal was measured at pH 1.2 (Stomach), pH 4.5 (Duodenum), pH 6.5 (Jejunum/Ileum), pH 7.4 (Blood) and pH 8.0 (Colon). The samples showed a significant difference of solubility at all pH values. Above pH 5 (pKa of Ketoprofen 4.08) the solubility increased considerably and thus two plots with different scale were required (see FIG. 12). The solubility of 1:1:1 Ketoprofen-Lysine-Gabapentin co-crystal was generally 2.5-fold higher than Ketoprofen Lysine co-crystal Form I. The Ketoprofen Lysine co-crystal Form I at pH 1.2 showed a solubility value of 0.1624±0.0016 mg/ml whereas the Ketoprofen-Lysine-Gabapentin of 0.4171±0.0312 mg/ml.

Table 10 below shows the solubility data obtained at the most representative pH of the GI tract.

TABLE 10

| Solubility at different pH (mg/ml) | | | | | |
|---|---|---|---|---|---|
| | pH 1.2 Stomach | pH 4.5 Duodenum | pH 6.5 Jejunum/ Ileum | pH 7.4 Blood | pH 8.0 Colon |
| Ketoprofen Lysine co-crystal Form I | 0.1624 ± 0.0016 | 0.5888 ± 0.0063 | 42.82 ± 0.4666 | 339 ± 3.6769 | 1349.5 ± 14.849 |
| 1:1:1 Ketoprofen-Lysine-Gabapentin co-crystal | 0.4171 ± 0.0312 | 1.513 ± 0.1117 | 110.05 ± 8.1317 | 871.2 ± 64.488 | 3354 ± 256.67 |

7. Stability Test

Samples of Ketoprofen-Lysine-Gabapentin (approx. 75 mg) were placed in glass vials crimped with a PTFE/silicone septum and stored at the desired temperature and humidity for the required time.

Controlled humidity was realized by using saturated solutions of salts: NaCl for 75% RH at 40° C. and NaBr for 60% RH at 25° C.

After the storage, the solid samples were analysed by XRPD analysis. Each stability test was performed in duplicate.

Stability of the samples was checked after 3 months.

Stability Test of Ketoprofen-Lysine-Gabapentin Co-Crystal

The stability of the Ketoprofen-Lysine-Gabapentin co-crystal was tested after storage for three months under controlled temperature and humidity conditions (sealed vial). The compound resulted to be stable at both tested conditions of 25° C. and 65% RH and of 40° C. and 75% RH.

Sample stability was assessed comparing the XRPD patterns of the solid samples collected after the stability tests with the diffractogram of the untreated sample.

Stability after storage at 25° C. and 60% RH The diffractograms of Ketoprofen-Lysine-Gabapentin samples stored at 25° C. and 60% RH in a sealed vial for 3 months showed that there were not significant differences in the XRPD patterns of the stored sample compared to the untreated starting material. The results of XRPD analysis confirmed that the solid state of the co-crystal remained unchanged during storage under accelerated conditions.

Stability after Storage at 40° C. and 75% RH

The diffractograms of Ketoprofen-Lysine-Gabapentin samples stored at 40° C. and 75% RH in a sealed vial for 3 months showed that there were not significant differences in the XRPD patterns of the stored sample compared to the untreated starting material. The results of XRPD analysis confirmed that the solid state of the co-crystal remained unchanged during storage under accelerated conditions.

8. In Vivo Studies

Inflammatory pain in rats induced by carrageenan intraplantar injection Male Wistar rats (270-280 g) (Envigo, Italy), were housed 2-3 per cage under controlled illumination (12:12 h light:dark cycle; light on 06.00 h) and standard environmental conditions (room temperature 22±1° C., humidity 60±10%) for at least 1 week before experimental use. Rat chow and tap water were available ad libitum. The procedures were approved by the Animal Ethics Committee of University of Campania "Luigi Vanvitelli". Animal care was in compliance with Italian Legislative Decree (D.L. 116/92) and European Commission Directive (O.J. of E.C. L358/1, 18/12/86) regulations on the protection of laboratory animals. All efforts were made to minimize animal suffering and the number of animals used.

Carrageenan-Induced Rat Paw Edema Test Method

Peripheral inflammatory pain was induced in the left hind paw of each animal by a single intraplantar injection of 1% A-carrageenan (100 µl for each rat in 0.9% NaCl). Vehicle (2 capsules Avicel PH101), Indomethacin (10 mg/kg, 100 µl), Ketoprofen Lysine co-crystal Form I (47.1 mg/kg, 1 capsule), Gabapentin (20.4 mg/kg, 2 ps), the admixture of Gabapentin and Ketoprofen Lysine co-crystal Form I (47.1 mg/Kg+20.4 mg/Kg, 2 capsules) and Ketoprofen-Lysine-Gabapentin co-crystal (67.5 mg/Kg, 2 capsules were orally administered 1 h before the carrageenan injection. The paw volume of the animals was measured by Plethysmometer (Ugo Basile, Varese, Italy) before (0 h) and after injection of carrageenan at different time intervals (1, 2, 3, 4, 5 and 6 h post-carrageenan). Edema was expressed as the mean increase in paw volume (ml) relative to control animals. The percentage inhibition of edema was calculated by the following equation:

$$\% \text{ inhibition of edema}=(Vc-Vt/Vc)\times 100,$$

where Vc is the edema volume in the control group and Vt is the edema volume in treated group.

The percentage inhibition of edema resulting from the above test is shown in the following Table 11:

TABLE 11

| % inhibition of edema | | | | | | |
|---|---|---|---|---|---|---|
| t | Vehicle | Indomethacin | Ketoprofen-Lysine | Gabapentin | Ketoprofen Lysine co-crystal Form I + Gabapentin | Ketoprofen-Lysine-Gabapentin |
| 0 | 0.68 +/− 0.02 | 0.67 +/− 0.01 | 0.65 +/− 0.02 | 0.68 +/− 0.02 | 0.64 +/− 0.06 | 0.66 +/− 0.02 |
| 1 | 1.02 +/− 0.06 | 1.16+/− 0.05 | 0.98 +/− 0.05 | 1.02 +/− 0.06 | 1.11 +/− 0.07 | 1.02 +/− 0.09 |
| 2 | 1.30 +/− 0.04 | 1.04 +/− 0.06 | 1.08 +/− 0.06 | 1.13 +/− 0.06 | 1.09 +/− 0.09 | 0.84 +/− 0.06 |
| 3 | 1.66 +/− 0.07 | 1.16+/− 0.08 | 1.25 +/− 0.1 | 1.39 +/− 0.1 | 1.21 +/− 0.04 | 0.93 +/− 0.07 |
| 4 | 1.95 +/− 0.18 | 1.11 +/− 0.07 | 1.39 +/− 0.17 | 1.76 +/− 0.12 | 1.18+/− 0.08 | 0.94 +/− 0.05 |
| 5 | 2.1 +/− 0.22 | 1.44 +/− 0.05 | 1.73 +/− 0.13 | 2.05 +/− 0.12 | 1.40 +/− 0.09 | 1.08 +/− 0.08 |

TABLE 11-continued

| % inhibition of edema | | | | | | |
|---|---|---|---|---|---|---|
| t | Vehicle | Indomethacin | Ketoprofen-Lysine | Gabapentin | Ketoprofen Lysine co-crystal Form I + Gabapentin | Ketoprofen-Lysine-Gabapentin |
| 6 | 2.29 +/− 0.14 | 1.64 +/− 0.05 | 1.95 +/− 0.12 | 2.26 +/− 0.11 | 1.60 +/− 0.02 | 1.37 +/− 0.11 |

t = time (hours)

Figure 13:
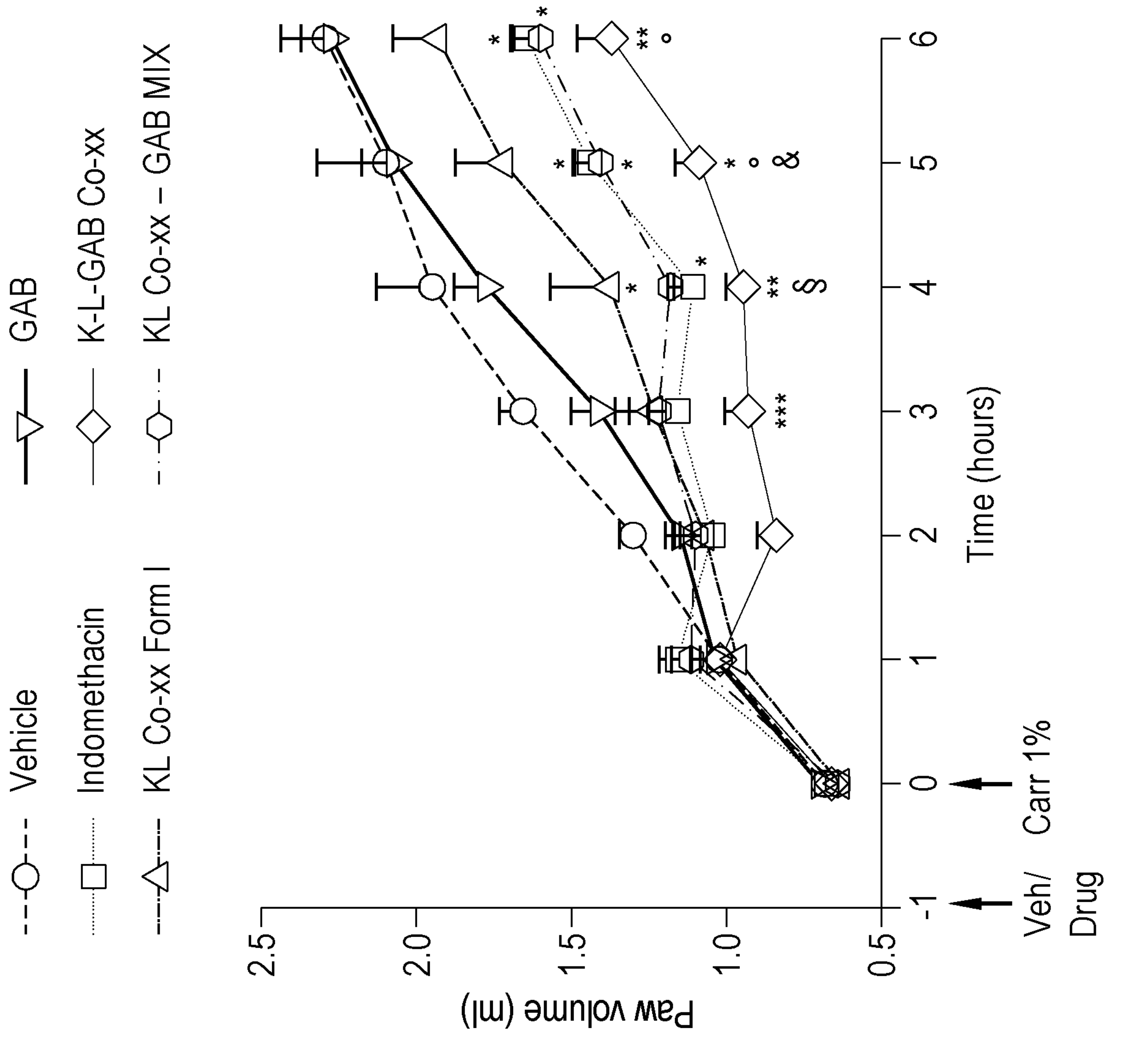
FIG. 13: graph of paw volume (ml) versus time (hours) in carrageenan-induced rat paw edema model after intraplantar injection of 1% of carrageenan followed by administration of Ketoprofen-Lysine-Gabapentin 1:1:1 co-crystal, of a 1:1 admixture of Ketoprofen Lysine co-crystal Form I and Gabapentin, of Ketoprofen Lysine co-crystal Form I, of Gabapentin, of Indomethacin or of Vehicle. Each time point or bar represents the mean±SEM of six (vehicle)/eight (drugs) rats. $P<0.05$ was considered as statistical significance and calculated by using two-way ANOVA followed by Bonferroni post-hoc test. *vs Vehicle, ○ vs Indomethacin, § vs 1:1 admixture of Ketoprofen Lysine co-crystal Form I and Gabapentin.
Figure 14:
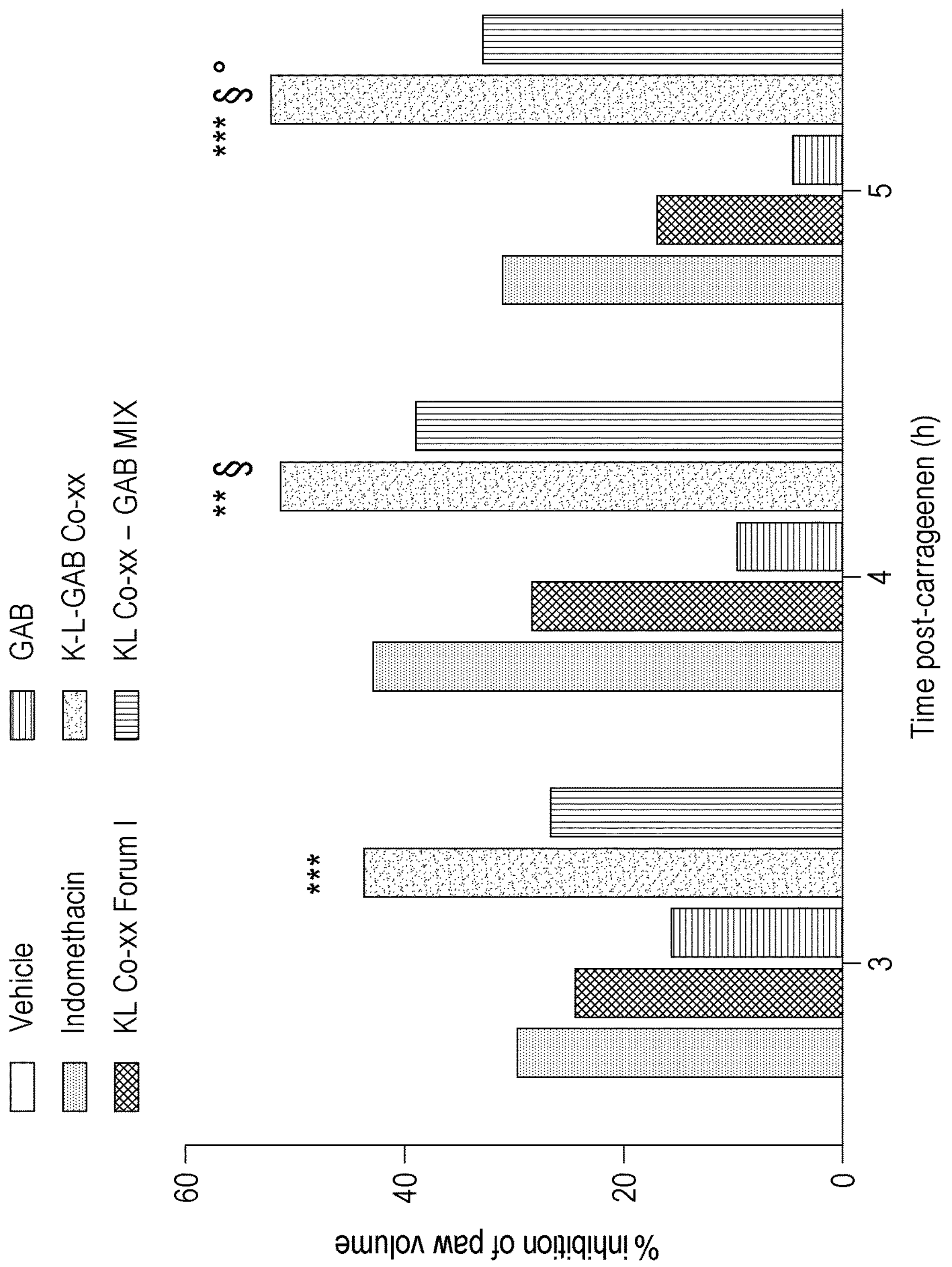
FIG. 14: bar chart of % inhibition of paw volume in carrageenan-induced rat paw edema model induced by Ketoprofen-Lysine-Gabapentin 1:1:1 co-crystal, by a 1:1 admixture of Ketoprofen Lysine co-crystal Form I and Gabapentin, by Ketoprofen Lysine co-crystal Form I, by Gabapentin, by Indomethacin or by Vehicle at 3, 4 and 5 hours post-carrageenan injection. Each time point or bar represents the mean±SEM of six (vehicle)/eight (drugs) rats. $P<0.05$ was considered as statistical significance and calculated by using two-way ANOVA followed by Bonferroni post-hoc test. *vs Vehicle, ○ vs Indomethacin, § vs 1:1 admixture of Ketoprofen Lysine co-crystal Form I and Gabapentin.
Figure 15:
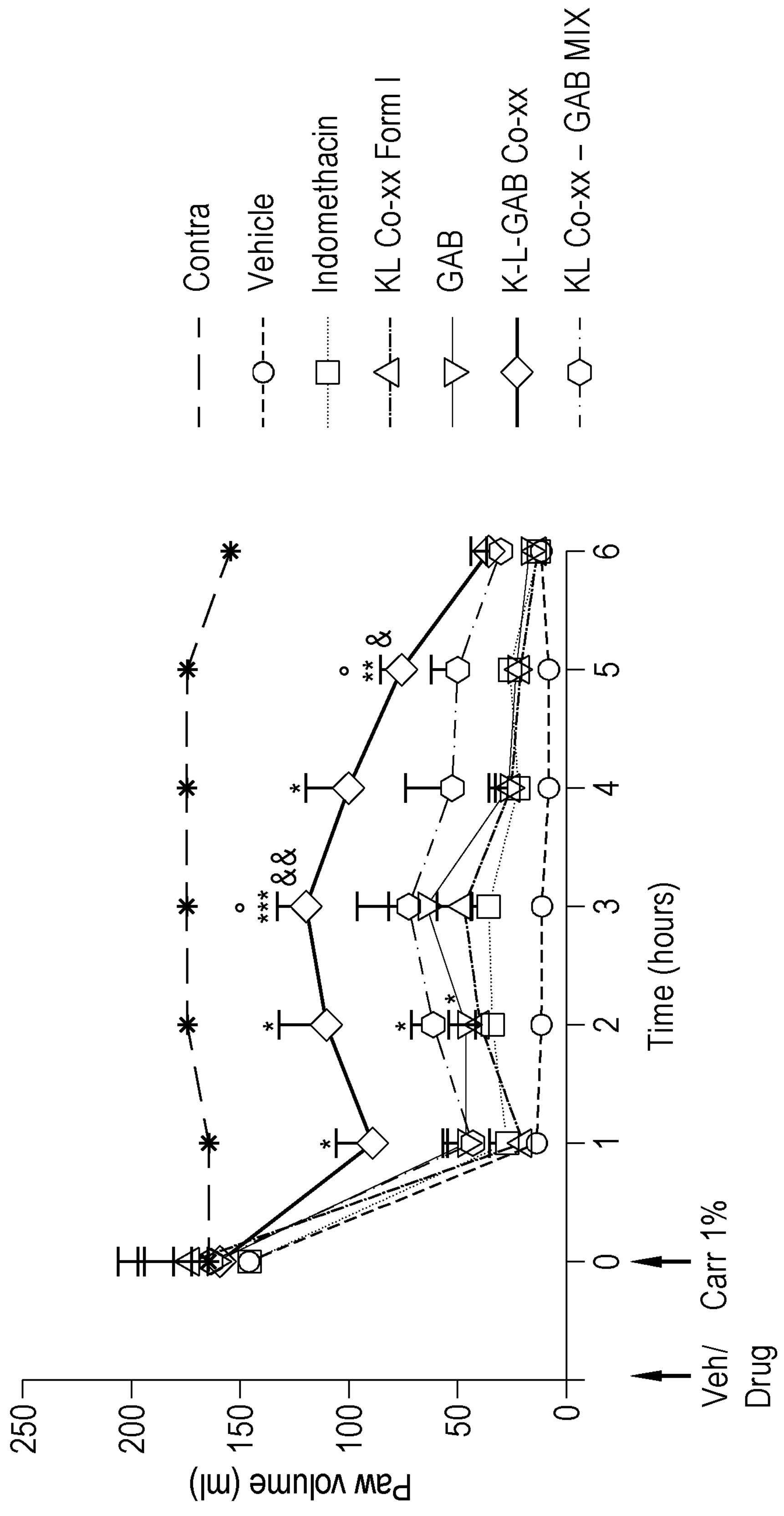
FIG. 15: graph of time-course of anti-inflammatory pain effect of Ketoprofen-Lysine-Gabapentin 1:1:1 co-crystal or Ketoprofen Lysine co-crystal Form I and GABA admixtures compared with Ketoprofen Lysine co-crystal Form I, Gabapentin, Indomethacin or Vehicle on rat withdrawal response (g) after intra-plantar injection of 1% of carrageenan. Each time point or bar represents the mean±SEM of six (vehicle)/eight (drugs) rats. $P<0.05$ was considered as statistical significance and calculated by using two-way ANOVA followed by Tukey's multiple comparison post-hoc test *vs Vehicle, § vs 1:1 admixture of Ketoprofen Lysine co-crystal Form I and Gabapentin, & vs Ketoprofen Lysine co-crystal Form I, ○vs Indomethacin.

The effect of the tested compounds on carrageenan-induced rat paw edema is represented in FIGS. 13 to 15.

In FIG. 13 is reported the time-course of the anti-inflammatory effect of 1:1:1 Ketoprofen-Lysine-Gabapentin co-crystal and of the 1:1 admixture of Gabapentin and Ketoprofen Lysine co-crystal Form I compared with Ketoprofen Lysine co-crystal Form I, Gabapentin, Indomethacin and Vehicle on rat paw swelling (paw volume in ml) after intra-plantar injection of 1% of carrageenan.

In FIG. 14 is reported the % inhibition of the paw volume induced by 1:1:1 Ketoprofen-Lysine-Gabapentin co-crystal and by Gabapentin and Ketoprofen Lysine co-crystal Form I in admixture compared with Ketoprofen Lysine co-crystal Form I, Gabapentin, Indomethacin and Vehicle at 3, 4 and 5 hours post-carrageenan injection. In the chart the value of the % of inhibition for the vehicle is zero.

FIG. 15 shows the time-course of anti-inflammatory pain effect of Ketoprofen-Lysine-Gabapentin 1:1:1 co-crystal or Ketoprofen Lysine co-crystal Form I and GABA admixtures compared with Ketoprofen Lysine co-crystal Form I, Gabapentin, Indomethacin or Vehicle on rat withdrawal response (g) after intra-plantar injection of 1% of carrageenan.

In the graphs of FIGS. 13 to 15, each time point or bar represents the mean±SEM of six rats per vehicle and eight rats per drug. $P<0.05$ was considered as statistical significance and calculated by using two-way ANOVA followed by Bonferroni post-hoc test. Keys: *vs vehicle, § vs KL Co-xx® GAB MIX, & vs KL Co-xx Form I, ○ vs Indomethacin.

From the graphs of FIGS. 13 and 15 appears that Ketoprofen Lysine co-crystal Form I, the admixture of Gabapentin and Ketoprofen Lysine co-crystal Form I and the 1:1:1 Ketoprofen-Lysine-Gabapentin co-crystal all attenuated carrageenan-evoked edema while Gabapentin was less effective.

Furthermore, it clearly results that the anti-inflammatory effect of the 1:1:1 Ketoprofen-Lysine-Gabapentin co-crystal of the invention was higher not only of the effect of the single actives Gabapentin and Ketoprofen Lysine but, unexpectedly, even higher of the effect of the two actives when administered together (synergic effect). The 1:1:1 Ketoprofen-Lysine-Gabapentin co-crystal of the invention clearly showed the synergistic effect and an increase of bioavailability, in comparison with the admixture of Gabapentin and Ketoprofen Lysine, or with Gabapentin or Ketoprofen Lysine alone.

It was also observed that the Ketoprofen-Lysine-Gabapentin co-crystal of the present invention appeared remarkably more potent than Indomethacin in this test. Finally, the more reclined curve of the Ketoprofen-Lysine-Gabapentin co-crystal of the present invention shown in FIG. 13, could be predictive of efficacy over an extended time period, longer than that of the individual actives given alone or even in admixture.

Comparative Effects of KSL-Gabapentin Co-Crystal and Gabapentin in the Model of Neuropathic Pain Induced by Nerve Ligation The testing substances were provided by the Dompe Farmaceutici S.p.A., Gabapentin was purchased from Spectrum (Cat #G1092), and the rice starch used in the vehicle control group was obtained from Sigma (Cat #S7260) in this project. Gabapentin (Spectrum (Cat #G1092)) alone or KSL-Gabapentin co-crystal were administrated orally via Torpac® Size 9 gelatine capsule(s). For each rat, 1-3 capsule (s) were given based on the proposed dosages. Gabapentin, serving as a positive control, was formulated in water for injection (WFI) for PO administration at a volume of 10 mL/kg.

Male Sprague Dawley rats weighing 180±20 g were provided by BioLasco Taiwan (under Charles River Laboratories Licensee). Space allocation for 2-3 animals was 45×25×21 cm. All animals were maintained in a controlled temperature (20-24° C.) and humidity (30%-70%) environment with 12 hr light/dark cycles. Free access to standard lab diet [MFG (Oriental Yeast Co., Ltd., Japan)] and autoclaved water were granted. All aspects of this work including housing, experimentation, and animal disposal were performed in general accordance with the "Guide for the Care and Use of Laboratory Animals: Eighth Edition" (National Academies Press, Washington, D.C., 2011) in our AAALAC-accredited laboratory animal facility. In addition, the animal care and use protocol was reviewed and approved by the IACUC at Pharmacology Discovery Services Taiwan, Ltd.

On Day 0, under pentobarbital sodium [50 mg/kg, intraperitoneally (IP)] anaesthesia, the left sciatic nerve was exposed at mid-thigh level. Four chromic gut ligatures, about 1 mm apart, were loosely tied around the nerve. The animals were then housed socially in cages with soft bedding for 13 days before the assessment for mechanical allodynia.

The rats were placed under inverted Plexiglas cages on a wire mesh rack and allowed to acclimate for 20 to 30 minutes. Mechanical allodynia threshold was assessed by the manual von Frey test using the Chaplan up/down method. The animals were given 20-30 minutes to acclimatize to the wire mesh rack in individual compartments prior to the behavioural testing. The paw was touched with a series of 8 manual von Frey monofilaments with logarithmically incremental stiffness [3.61 (0.4 g), 3.84 (0.6 g), 4.08 (1.0 g), 4.31 (2.0 g), 4.56 (4.0 g), 4.74 (6.0 g), 4.93 (8.0 g), and 5.18 (15.0 g)]. The manual von Frey monofilament was applied perpendicularly from underneath the mesh floor to the central plantar surface with sufficient force to cause a slight buckling against the paw, and held for approximately 6-8 seconds. A positive response was noted if the paw was sharply withdrawn; ambulation was considered an ambiguous response, and in such cases, the stimulus was reapplied.

Mechanical threshold [50% withdrawal threshold (g)] was assessed using the up/down method following the procedure described by Chaplan (1994).

The resulting pattern of positive and negative responses was tabulated using the convention, X=withdrawal; 0=no withdrawal and the 50% response threshold was interpolated using the formula: Mechanical threshold=(10 [Xf+kδ])/10, 000, where Xf=value (in log units) of the final von Frey hair used; k=tabular value for the pattern of positive/negative responses; and δ=mean difference (in log units) between stimuli (here, 0.224).

All rats were assessed for mechanical allodynia for pre-surgical allodynia thresholds on Day −1 (pre-surgery baseline). The rats were pre-selected for experimentation only if the pain threshold on Day 13 after nerve ligation (pre-treatment) was reduced by 10 g of force relative to the response of the individual paw before nerve ligation (pre-surgery), namely, with clear presence of allodynia. The rats were randomized based on pre-dose mechanical allodynia scores to balanced treatment groups. The compounds were administered orally (PO) by the size 9 gelatin capsule(s) or in the proposed formulation. The mechanical allodynia was assessed again at 1, 3 and 6 hour(s) following administration of the test article, vehicle or reference compound on Day 14 post-surgery.

Figure 16:
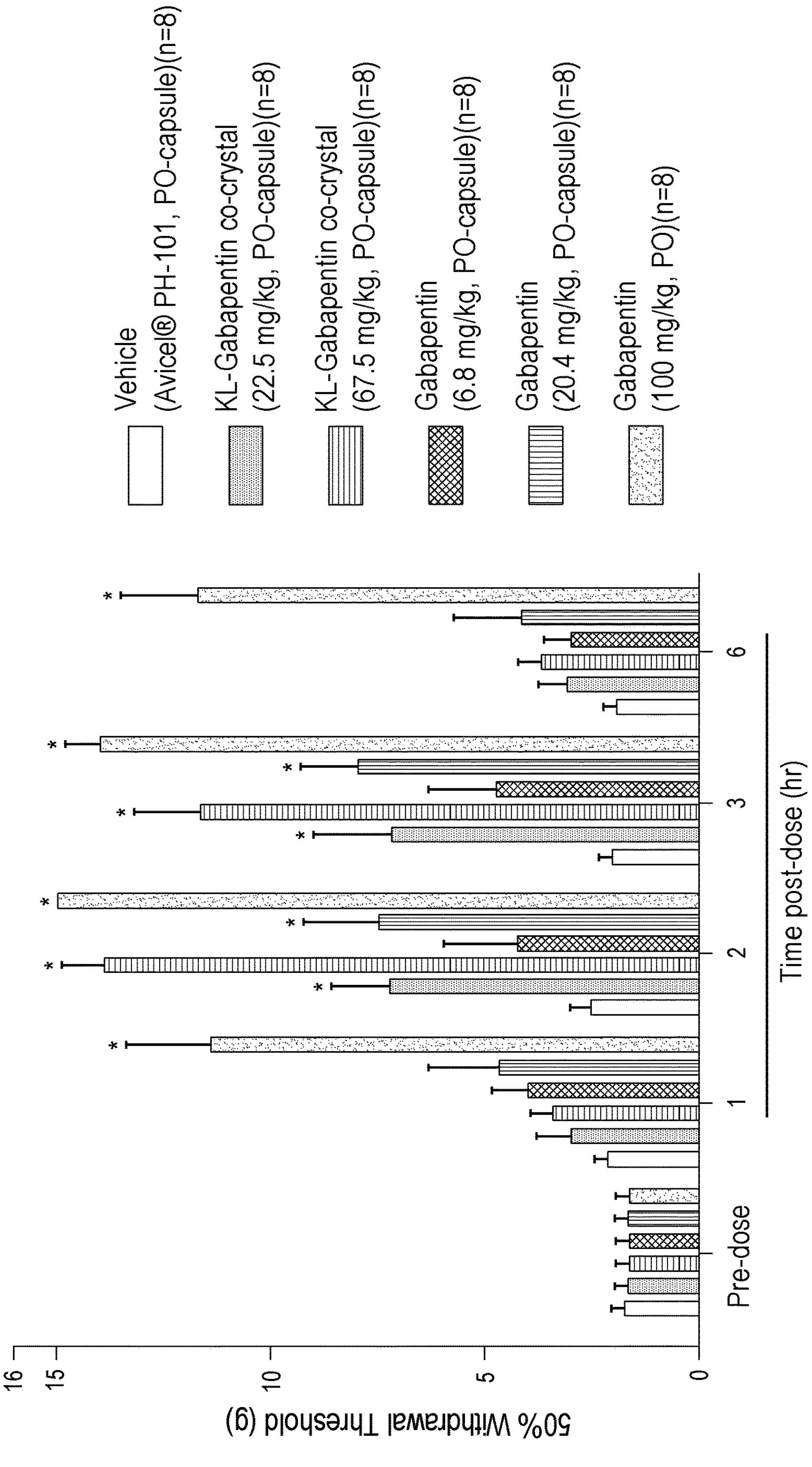
FIG. 16: bar chart of the effect of treatment with different dosages of the Ketoprofen-Lysine-Gabapentin 1:1:1 co-crystal of the invention and of Gabapentin compared to vehicle on mechanical allodynia, measured as 50% withdrawal threshold (g), at 1, 2, 3 and 6 hours after administration. All values represent mean±standard error of the mean (SEM) in the individual groups. One-way ANOVA followed by Dunnett's test was applied for comparison between the groups. For Ketoprofen-Lysine-Gabapentin 1:1:1 co-crystal, significance was considered at the $p<0.05$ level vs Gabapentin and vs vehicle group. For Gabapentin group, significance was considered at the $p<0.05$ level vs vehicle group. The statistical analysis was performed by GraphPad Prism 5.0.

The results are shown in FIG. 16.

All values represent mean±standard error of the mean (SEM) in the individual groups. One-way ANOVA followed by Dunnett's test was applied for comparison between the vehicle control and compound-treated groups. Significance was considered at the $p<0.05$ level. The statistical analysis was performed by GraphPad Prism 5.0.

FIG. 16 clearly shows the synergistic effect of the co-crystal of the invention at 2 and 3 hours post dose.

Determination of the Exposure in Plasma and Brain of KLS and Gabapentin after their Oral Administration as Capsules in the Rats Aim of the study was the determination of the brain penetration of Gabapentin in KLS-Gabapentin Co-crystal compared to the physical mixture of KLS and so Gabapentin and Gabapentin alone after administration in capsules in the rats.

Sprague Dawley male rat (body weights 310 gr at the time of the treatment) were used in this study. The animals were originally supplied by Harlan, Italy. Once receipt from the supplier, the animals were subjected to health examinations and acceptance. The animals were housed, in a group of three, in cages suitable for the species and were routinely kept in the following environment except for short periods of time where experimental procedures dictated otherwise. The animals were acclimatized to local housing conditions for approximately 5 days.

The animals were housed in a single, exclusive room, air conditioned to provide a minimum of 15 air changes/hour. The environmental controls were set to maintain temperature within the range 22° C. and relative humidity within the range 50 to 60% with an approximate 12 hour light and 12 hour dark cycle that is controlled automatically. Food (Mucedola Standard GLP diet) and water were available ad libitum throughout the study. All animals were weighed on the day of each treatment. Clinical signs were monitored at regular intervals throughout the study in order to assess any reaction to treatment. Each animal was uniquely identified with a coloured spray on the back before the experiment.

At the end of the study animals were sacrificed by exsanguination under anaesthesia.

The experiment was carried on in agreement with the Italian Law D. L.vo 4 marzo 2014, n. 26.

The experimental protocol consisted in the blood and brain tissue sampling on the animals according to the following Tables 12 and 13 and analysis of samples as described below.

TABLE 12

| Blood Sampling | |
|---|---|
| Animals/Time Point | 7 time points |
| Time points | 30 min, 1, 2, 3, 6, 8, and 24 h |
| Fasting Requirements | Not required |
| Collection Site | Animals will be exsanguinated from caudal vein |
| Collection tube | Li heparin anticoagulant |
| Target Blood Volume | 70 µL |
| Sample Identification | Label indicating: Study number, animal ID, test item ID, sampling time |
| Sample Requirements | Stored in ice and centrifuged at +4° C., 3000 g for 10 minutes |
| Final Sample Storage Conditions | −20° C. until bioanalysis |

TABLE 13

| Brain tissue sampling | |
|---|---|
| Sampling schedule | Serial sampling |
| Time Point | 2 time points |
| Time points | 2 and 24 hr |
| Fasting Requirements | Not required |
| Sample treatment | Brains are washed in saline, dried and weighted and place in tubes. |
| Sample Identification | Label indicating: Study number, animal ID, test item ID, sampling time |
| Sample Requirements | Stored in ice and centrifuged at +4° C., 3000 g for 10 minutes |
| Final Sample Storage Conditions | −20° C. until bioanalysis |

Stock solutions of Ketoprofen and Gabapentin were prepared at 1 mg/mL in MeOH and a mix stock solution was prepared by dilution of the two mentioned before to reach a final concentration of 100 µg/mL of each analyte. Stock solutions of DF1681Y and Gabapentin Impurity A were prepared respectively at 2 mg/mL and 1 mg/mL in MeOH. A mixture of the two was prepared in ACN with a final so concentration of 5000 and 500 ng/mL respectively (mix IS).

Calibration curve and QC samples were prepared in rat blank plasma by adding 2 µL of each stock solution to 18 µL plasma. Spiked plasma samples were added to 200 µL of mix_IS and centrifuged for 5 min at 9000 g at 5° C. Samples from the oral treatments were prepared diluted 1:10 in blank plasma and 20 µL of the diluted plasma were processed as described above. 100 µL of extracted samples were then diluted 120 µL of mobile phase A.

Brain collected were homogenized in ammonium formiate 10 mM buffer 1 g/5 mL. Samples as well calibrants and QC samples were prepared by adding 20 µL of brain homogenate to 200 µL of mix_IS and centrifuged for 5 min at 9000 g at 5° C. 100 µL of extracted samples were then diluted 120 µL of mobile phase A.

Rat plasma levels of Ketoprofen and Gabapentin were measured after administration of two capsules of the co-crystal KLS-Gabapentin and physical mixture of the two analytes. Concentrations in plasma and brain are reported in FIGS. 17 to 19.

Figure 17:
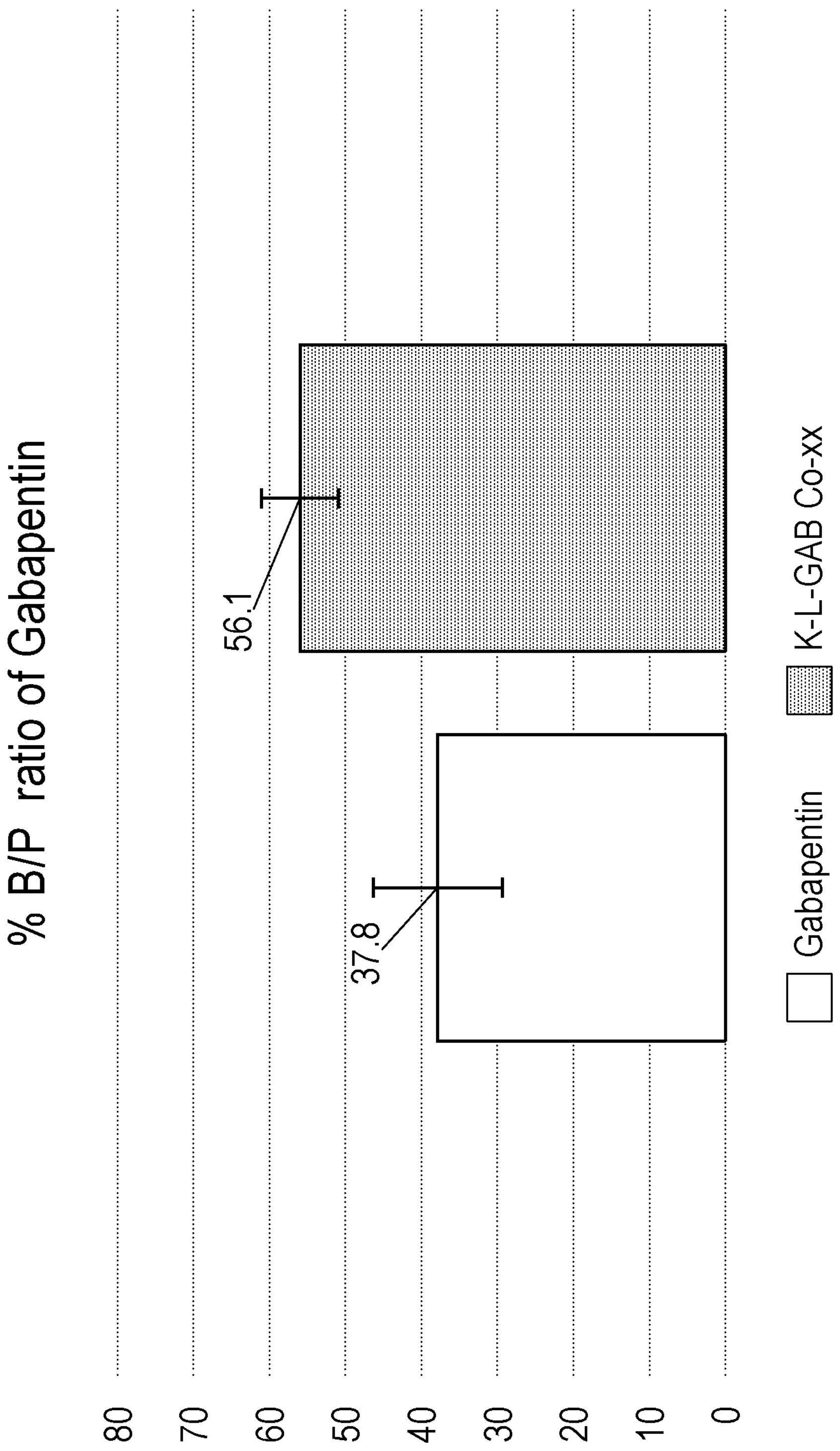
FIG. 17: Brain penetration ratio (brain/plasma %) of Gabapentin, when administrated orally alone and as Ketoprofen-Lysine-Gabapentin 1:1:1 co-crystal.

Brain and plasma concentrations of the two compounds were assessed after 2 hr so resulting in a brain/plasma penetration ratio of 37.8% for gabapentin when administrated alone versus 56.1% when administrated as KLS-Gabapentin co-crystal (FIG. 17). Significance was considered at the $p<0.05$ level. Interestingly, the brain and plasma levels of Gabapentin and Ketoprofen observed in KLS-Gabapentin co-crystal were statistically significative higher ($p<0.05$) compared to the KLS Gabapentin mixture (FIGS. 18 and 19).

Figure 18:
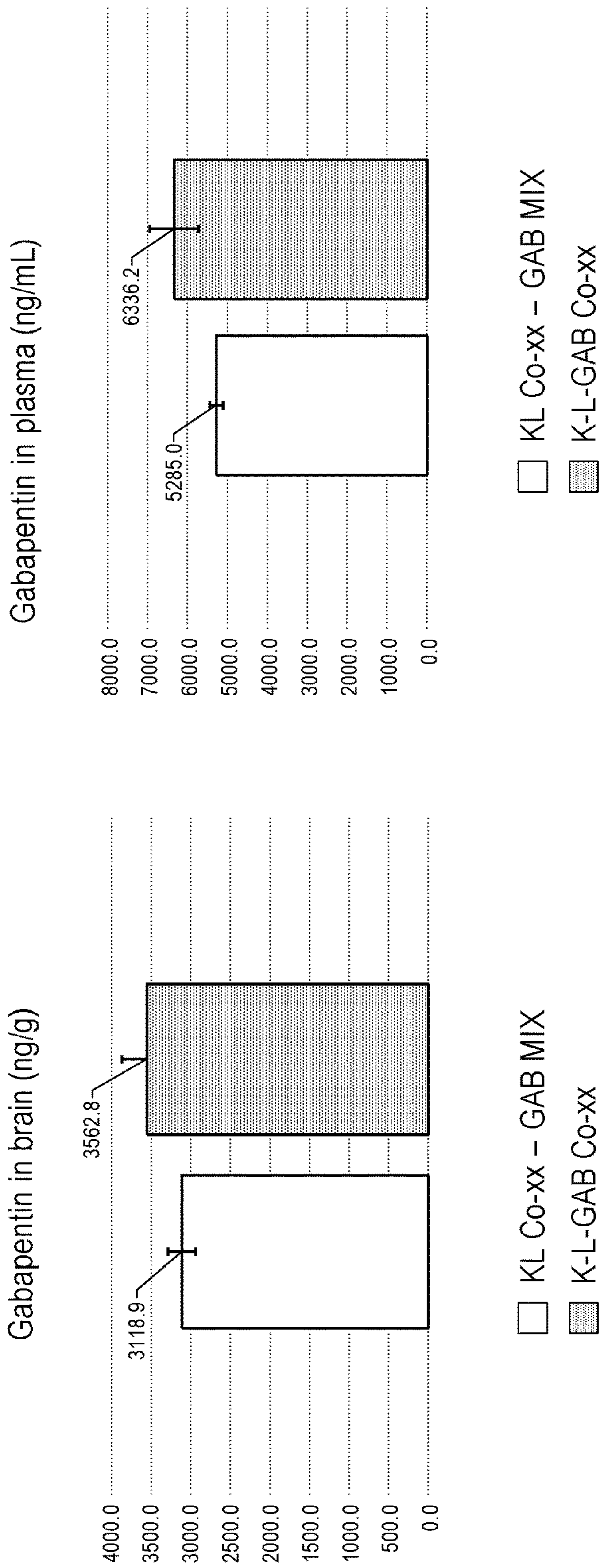
FIG. 18: Gabapentin concentration in brain and plasma, when administrated as physical mixture (MIX) of Gabapentin and Ketoprofen Lysine co-crystal Form I or as Ketoprofen-Lysine-Gabapentin 1:1:1 co-crystal.
Figure 19:
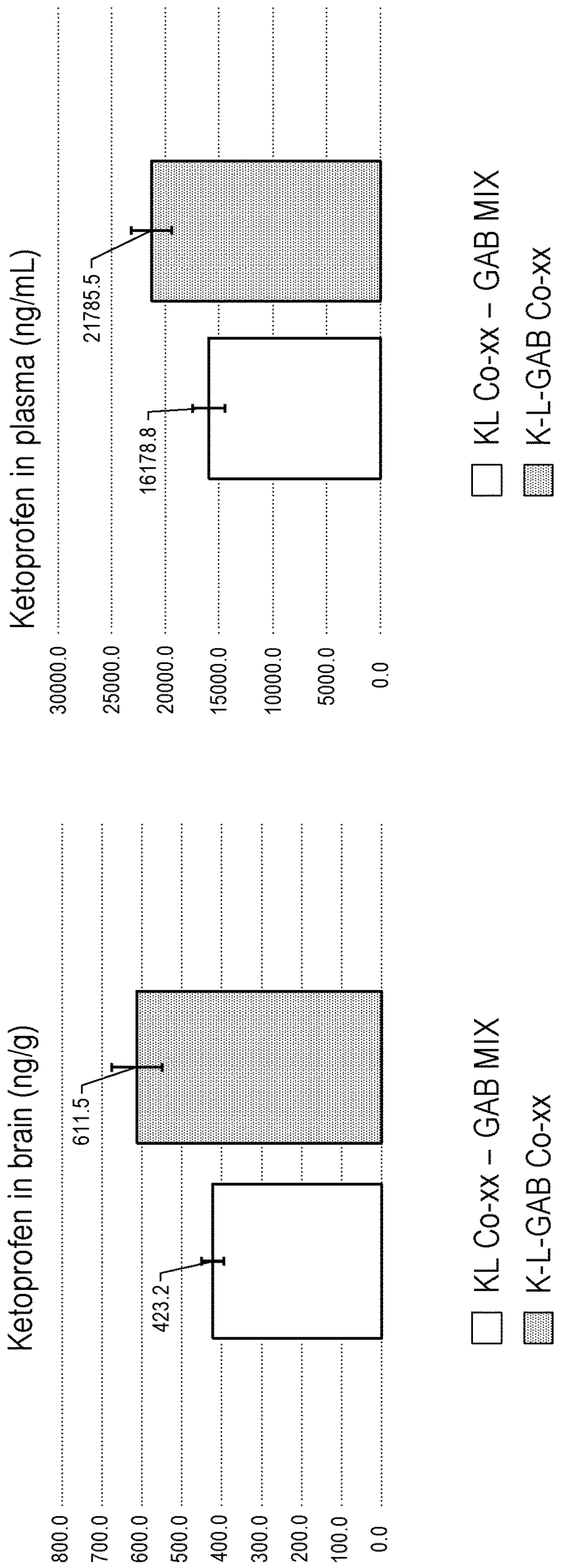
FIG. 19: Ketoprofen concentration in brain and plasma, when administrated as physical mixture (MIX) of Gabapentin and Ketoprofen Lysine co-crystal Form I or as Ketoprofen-Lysine-Gabapentin 1:1:1 co-crystal.

FIGS. 18 and 19 clearly show the concentration increase of the Ketoprofen from the Co-crystal of the present invention in brain and plasma when compared with the admixture of Gabapentin and Ketoprofen Lysine due to a better bioavailability.

The invention claimed is:

1. A co-crystal of Gabapentin, Ketoprofen and Lysine wherein the molar ratio of the components is 1:1:1, and wherein the co-crystal is characterized by the following XRPD diffraction peaks: 3.6, 9.5, 9.6, 18.5 and 20.0 degrees 2-theta±0.2 degrees 2-theta.

2. The co-crystal according to claim 1, further characterized by the following XRPD diffraction peaks: 15.4, 17.8, 21.0, 21.8 and 24.2 degrees 2-theta±0.2 degrees 2-theta.

3. The co-crystal according to claim 1, further characterized by one or more of the following:

a DSC thermogram with the endothermic peak corresponding to the melting point at about 141.4° C. as shown in FIG. 2;

a TGA thermogram as shown in FIG. 5;

an FT Raman spectrum which exhibits the following absorption bands:

| Position ($cm^{-1}$) | intensity |
|---|---|
| 272 | 14.482 |
| 290 | 15.262 |
| 350 | 8.548 |
| 373 | 9.146 |
| 410 | 12.010 |
| 507 | 9.469 |
| 618 | 16.350 |
| 711 | 18.962 |
| 723 | 15.118 |
| 759 | 9.965 |
| 783 | 8.629 |
| 820 | 8.798 |
| 884 | 15.143 |
| 912 | 10.347 |
| 976 | 15.373 |
| 1001 | 116.397 |
| 1032 | 22.031 |
| 1056 | 15.102 |
| 1265 | 15.288 |
| 1281 | 19.151 |
| 1315 | 17.851 |
| 1346 | 12.275 |
| 1362 | 12.462 |
| 1396 | 15.608 |
| 1449 | 40.732 |
| 1490 | 8.848 |
| 1598 | 97.480 |
| 1652 | 58.327 |
| 2723 | 9.298 |
| 2771 | 11.471 |
| 2863 | 55.705 |
| 2929 | 93.607 |
| 2967 | 51.194 |
| 3005 | 21.687 |
| 3064 | 78.264; |

an FT-IR spectrum which exhibits the following absorption bands:

| Position ($cm^{-1}$) | intensity |
|---|---|
| 420 | 61.320 |
| 479 | 86.959 |
| 496 | 84.511 |
| 508 | 83.197 |
| 556 | 78.060 |
| 579 | 84.959 |
| 603 | 85.297 |
| 619 | 82.829 |
| 641 | 75.429 |
| 654 | 84.715 |
| 691 | 65.138 |
| 700 | 62.820 |
| 709 | 62.038 |
| 741 | 86.760 |
| 777 | 84.071 |
| 828 | 88.929 |
| 841 | 90.789 |
| 881 | 80.755 |
| 910 | 87.977 |
| 928 | 88.449 |
| 944 | 88.718 |
| 963 | 87.854 |
| 999 | 90.389 |
| 1028 | 89.041 |
| 1060 | 86.249 |
| 1076 | 87.549 |
| 1089 | 86.128 |
| 1114 | 90.673 |
| 1142 | 85.854 |
| 1158 | 83.571 |
| 1179 | 85.407 |
| 1204 | 85.563 |
| 1243 | 72.908 |
| 1281 | 63.418 |
| 1317 | 73.752 |
| 1359 | 64.089 |
| 1391 | 54.270 |
| 1426 | 78.288 |
| 1450 | 71.708 |
| 1474 | 67.220 |
| 1501 | 58.164 |
| 1508 | 57.858 |
| 1542 | 63.709 |
| 1578 | 74.234 |
| 1596 | 77.930 |
| 1628 | 69.686 |
| 1649 | 74.257 |
| 2600 | 83.830 |
| 2850 | 79.325 |
| 2929 | 76.320; |

a $^{1}H$-NMR spectrum exhibiting the solution $^{1}H$-NMR signals as shown in FIG. 8; and a solid state $^{13}C$ CPMAS spectrum exhibiting the $^{13}C$ CPMAS signals as shown in FIGS. 9 to 11.

4. The co-crystal according to claim 1, wherein the Ketoprofen is (S)-Ketoprofen.

5. The co-crystal according to claim 1, wherein the Lysine is (S)-Lysine.

6. A method for the prevention, reduction or treatment of pain and/or inflammation in a subject in need thereof, comprising administration of the co-crystal according to claim 1, alone or in combination with one or more physiologically acceptable excipients.

7. The method according to claim 6, wherein the pain is acute or chronic pain.

8. The method according to claim 6, wherein the pain is selected from headache, toothache, menstrual pain, muscle pain, neuropathic pain, pain associated to neuroinflammation, diabetic neuropathy, cancer pain, osteoarthritis, low back pain, sciatalgia, fibromyalgia, trigeminal neuralgia, post-surgical and post-operative pain, post herpetic neuralgia, rheumatoid arthritis, ankylosing spondylitis, frozen shoulder, phantom limb pain or HIV pain.

9. A pharmaceutical composition comprising the co-crystal according to claim 1 and a least one pharmaceutically acceptable excipient.

10. The pharmaceutical composition according to claim 9, which contains 0.5-60% by weight of the co-crystal and 40-99.5% by weight of one or more pharmaceutically acceptable excipients.

11. The pharmaceutical composition according to claim 9 which is a solid composition for oral administration.

12. The pharmaceutical composition according to claim 10, which is a solid composition for oral administration.

13. A process for the preparation of the co-crystal according to claim 1, which comprises:

a) suspending Gabapentin, Ketoprofen and Lysine in a suitable solvent, b) dissolving Gabapentin, Ketoprofen and Lysine, optionally by heating the suspension, optionally under stirring, till a clear solution is obtained, c) subsequently cooling the solution, and d) optionally adding an anti-solvent.

14. The process according to claim 13, wherein the Ketoprofen and Lysine in step a) are in form of a Ketoprofen Lysine salt or a co-crystal.

15. The process according to claim 13, wherein the Ketoprofen is the free acid and/or said Lysine is in neutral form.

16. The process according to claim 13, wherein the Gabapentin is in neutral form.

* * * * *